(12) United States Patent
Sawada et al.

(10) Patent No.: US 9,312,496 B2
(45) Date of Patent: *Apr. 12, 2016

(54) ORGANIC ELECTROLUMINESCENT ELEMENT

(75) Inventors: Yuichi Sawada, Kitakyushu (JP);
Masanori Hotta, Kitakyushu (JP);
Megumi Matsumoto, Kitakyushu (JP)

(73) Assignee: NIPPON STEEL & SUMIKIN CHEMICAL CO., LTD., Tokyo (JP)

( * ) Notice: Subject to any disclaimer, the term of this patent is extended or adjusted under 35 U.S.C. 154(b) by 330 days.

This patent is subject to a terminal disclaimer.

(21) Appl. No.: 13/878,608

(22) PCT Filed: Oct. 3, 2011

(86) PCT No.: PCT/JP2011/072784
§ 371 (c)(1),
(2), (4) Date: Apr. 10, 2013

(87) PCT Pub. No.: WO2012/050003
PCT Pub. Date: Apr. 19, 2012

(65) Prior Publication Data
US 2013/0193429 A1    Aug. 1, 2013

(30) Foreign Application Priority Data

Oct. 13, 2010   (JP) .................. 2010-230313

(51) Int. Cl.
| | | |
|---|---|---|
| H01L 51/50 | (2006.01) | |
| H01L 51/00 | (2006.01) | |
| C07D 487/04 | (2006.01) | |
| C07D 519/00 | (2006.01) | |
| C09K 11/06 | (2006.01) | |
| H05B 33/20 | (2006.01) | |

(52) U.S. Cl.
CPC .......... *H01L 51/0071* (2013.01); *C07D 487/04* (2013.01); *C07D 519/00* (2013.01); *C09K 11/06* (2013.01); *H01L 51/0072* (2013.01); *H05B 33/20* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *H01L 51/0081* (2013.01); *H01L 51/0085* (2013.01); *H01L 51/5016* (2013.01)

(58) Field of Classification Search
None
See application file for complete search history.

(56) References Cited

U.S. PATENT DOCUMENTS 8,766,249 B2 *  7/2014  Sawada et al. ............ 257/40
2006/0216411 A1 *  9/2006  Steudel et al. ............ 427/66
2008/0297034 A1 * 12/2008  Abe et al. ................ 313/504
2010/0141126 A1 *  6/2010  Otsu et al. ............... 313/504
2012/0273764 A1    11/2012  Yu et al.

FOREIGN PATENT DOCUMENTS

| JP | 2009-54809 A | | 3/2009 |
|---|---|---|---|
| JP | 2009054809 | * | 3/2009 |
| JP | 2009-182034 A | | 8/2009 |
| JP | 2010040829 | * | 2/2010 |
| JP | 2010040829 A | * | 2/2010 |
| JP | 2010-177644 A | | 8/2010 |
| WO | WO-2010/041687 A1 | | 4/2010 |
| WO | WO-2011/055933 A2 | | 5/2011 |
| WO | WO 2011132866 A1 | * | 10/2011 |

OTHER PUBLICATIONS

International Search Report for the Application No. PCT/JP2011/072784 mailed Nov. 22, 2011.

(Continued)

*Primary Examiner* — Jennifer Chriss
*Assistant Examiner* — Dylan Kershner
(74) *Attorney, Agent, or Firm* — Cheng Law Group, PLLC

(57) ABSTRACT

Provided are a novel nitrogen-containing aromatic heterocyclic compound and an organic electronic device using the compound. Specifically provided is an organic electroluminescent device, including a plurality of organic layers between an anode and a cathode laminated on a substrate, in which at least one of the organic layers contains a nitrogen-containing aromatic compound represented by the following formula (1). In the formula, L represents an n+m-valent group arising from an alkane, a cycloalkane, an aromatic hydrocarbon, an aromatic heterocyclic compound, a triarylamine, or a diarylsulfone, A represents an alkyl group, a cycloalkyl group, an alkenyl group, an alkynyl group, a silyl group, an acyl group, an aromatic hydrocarbon group, or an aromatic heterocyclic group, X represents $C(R)_2$, oxygen, S, or Se, R represents H, an alkyl group, a cycloalkyl group, an alkenyl group, an alkynyl group, an aromatic hydrocarbon group, or an aromatic heterocyclic group, m represents an integer of 1 to 4, and n represents an integer of 0 to 3. The total number of m and n is 2 to 4.

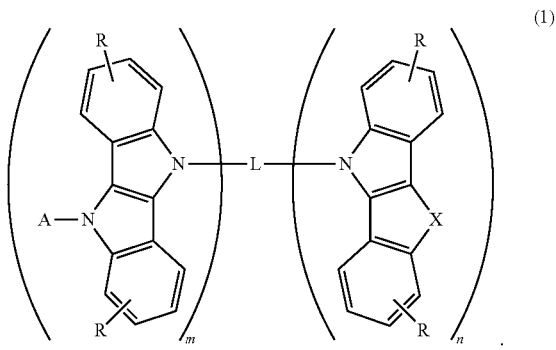

(1)

10 Claims, 1 Drawing Sheet

(56) References Cited

OTHER PUBLICATIONS

English Translation of International Preliminary Report on Patentability for the Application No. PCT/JP2011/072784 mailed May 16, 2013.

Jin, Youngeup et al., "New Conjugated Polymer Based on Dihydroindoloindole for LEDs", Bull. Korean Chem. Soc., 2006, vol. 27, No. 7. pp. 1043-1047.

Dorin, S. et al., "Photophysics of *trans*-stilbene analogues: indolo[3,2-*b*] indole and its heterosubstituted sulfur and selenium derivatives", Chemical Physics, 1997, vol. 216, No. I,2, pp. 179-192.

* cited by examiner

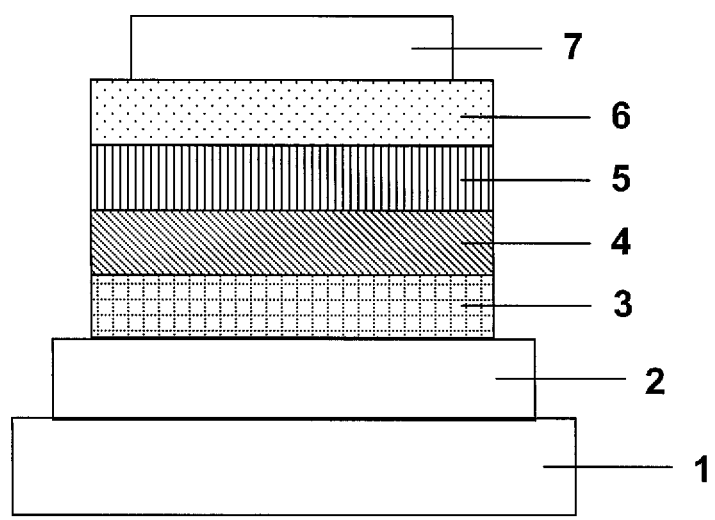

ORGANIC ELECTROLUMINESCENT ELEMENT

TECHNICAL FIELD

The present invention relates to an organic electroluminescent device containing a nitrogen-containing aromatic compound, and more specifically, to a thin-film-type device that emits light when an electric field is applied to a light-emitting layer formed of an organic compound.

BACKGROUND ART

In general, an organic electroluminescent device (hereinafter referred to as organic EL device) is constructed of a light-emitting layer and a pair of counter electrodes interposing the light-emitting layer therebetween in its simplest structure. That is, the organic EL device uses the phenomenon that, when an electric field is applied between both the electrodes, electrons are injected from a cathode and holes are injected from an anode, and each electron and each hole recombine in the light-emitting layer to emit light.

In recent years, progress has been made in developing an organic EL device using an organic thin film. In order to enhance luminous efficiency particularly, the optimization of the kind of electrodes has been attempted for the purpose of improving the efficiency of injection of carriers from the electrodes. As a result, there has been developed a device in which a hole-transporting layer formed of an aromatic diamine and a light-emitting layer formed of an 8-hydroxyquinoline aluminum complex (hereinafter referred to as Alq3) are provided between electrodes as thin films, resulting in a significant improvement in luminous efficiency, compared with conventional devices in which a single crystal of anthracene molecules or the like is used. Thus, the development of the above-mentioned organic EL device has been promoted in order to accomplish its practical application to a high-performance flat panel having features such as self-luminescence and rapid response.

Further, studies have been made on using phosphorescent light rather than fluorescent light as an attempt to raise the luminous efficiency of a device. Many kinds of devices including the above-mentioned device in which a hole-transporting layer formed of an aromatic diamine and a light-emitting layer formed of Alq3 are provided emit light by using fluorescent light emission. However, by using phosphorescent light emission, that is, by using light emission from a triplet excited state, luminous efficiency is expected to be improved by about three times to four times, compared with the case of using conventional devices in which fluorescent light (singlet) is used. In order to accomplish this purpose, studies have been made on adopting a coumarin derivative or a benzophenone derivative as a light-emitting layer, but extremely low luminance has only been provided. Further, studies have been made on using a europium complex as an attempt to use a triplet state, but highly efficient light emission has not been accomplished. In recent years, many studies on a phosphorescent light-emitting dopant material centered on an organic metal complex such as an iridium complex have been made, as described in Patent Literature 1, for the purpose of attaining the high efficiency and long lifetime of light emission.

CITATION LIST

Patent Literature

[PTL 1] JP 2003-515897 T
[PTL 2] JP 2001-313178 A
[PTL 3] JP 2009-054809 A
[PTL 4] JP 2010-040829 A
[PTL 5] JP 2010-205815 A

In order to obtain high luminous efficiency, host materials that are used with the dopant materials described above play an important role. Typical examples of the host materials proposed include 4,4'-bis(9-carbazolyl)biphenyl (hereinafter referred to as CBP) as a carbazole compound disclosed in Patent Literature 2. When CBP is used as a host material for a green phosphorescent light-emitting material typified by a tris(2-phenylpyridine) iridium complex (hereinafter referred to as Ir(ppy)$_3$), a charge balance is disturbed because CBP has the characteristic of facilitating the delivery of holes and not facilitating the delivery of electrons. Thus, excessively delivered holes flow out into an electron-transporting layer side, with the result that the luminous efficiency from Ir (ppy)3 lowers.

In order to provide high luminous efficiency to an organic EL device, it is necessary to use a host material, which has high triplet excitation energy, and is striking a good balance in both charge (hole and electron)-injecting/transporting property. Further desired is a compound, which has electrochemical stability, has high heat resistance, and has excellent amorphous stability, and hence further improvement has been demanded.

Patent Literature 3 discloses such an indoloindole compound as shown below. However, the application of the compound is limited to an organic transistor material and the literature does not disclose its usefulness as an organic EL material, in particular, a phosphorescent host material.

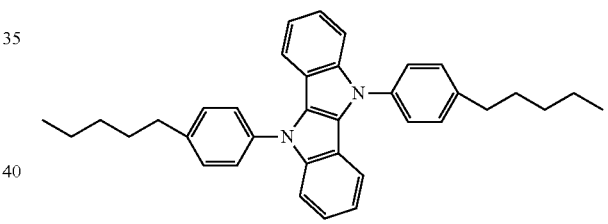

In addition, Patent Literatures 4 and 5 disclose organic EL devices using such compounds as shown below.

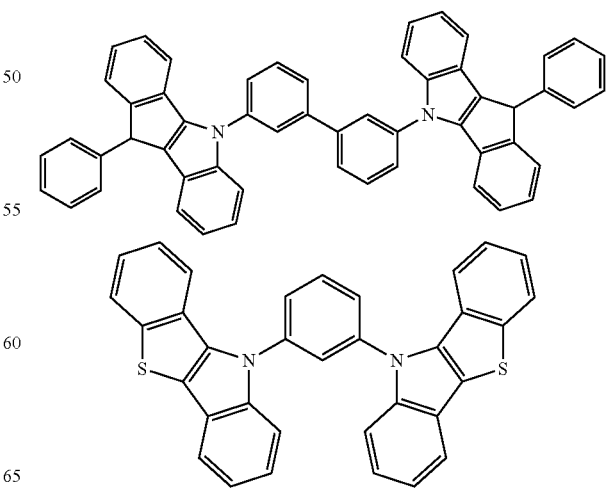

However, each of the literatures merely discloses a material having, in the same molecule, partial structures in each of which a five-membered aromatic heterocycle containing a chalcogen atom as a ring-forming atom is fused, and none of the literatures specifically describes a material having, in the same molecule, an indolo[3,2-b]indole skeleton and a four-ring fused heterocycle having indole in a partial structure thereof.

SUMMARY OF INVENTION

In order to apply an organic EL device to a display device in a flat panel display or the like, it is necessary to improve the luminous efficiency of the device and also to ensure sufficiently the stability in driving the device. The present invention has an object to provide, in view of the above-mentioned circumstances, an organic EL device, which has high efficiency, has high driving stability, and is practically useful and a compound suitable for the organic EL device.

The inventors of the present invention have made extensive studies, and as a result, have found that when a nitrogen-containing aromatic compound having a specific structure is used in an organic electronic device, a charge mobility increases. Thus, the inventors have completed the present invention.

The present invention relates to an organic electroluminescent device, including an anode, a plurality of organic layers, and a cathode laminated on a substrate, in which at least one of the organic layers contains a nitrogen-containing aromatic compound represented by the general formula (1).

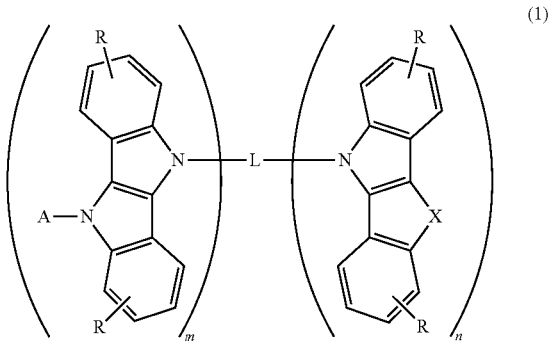

(1)

In the formula, L represents an n+m-valent group arising from an alkyl group having 1 to 30 carbon atoms, an n+m-valent group arising from a cycloalkyl group having 3 to 30 carbon atoms, an n+m-valent aromatic hydrocarbon group having 6 to 50 carbon atoms, an n+m-valent aromatic heterocyclic group having 3 to 50 carbon atoms and free of a fused heterocycle having 4 or more rings, or an n+m-valent group arising from a triarylamine having 9 to 30 carbon atoms or from a diarylsulfone having 6 to 24 carbon atoms, A's each independently represent an alkyl group having 1 to 30 carbon atoms, a cycloalkyl group having 3 to 30 carbon atoms, an alkenyl group having 2 to 30 carbon atoms, an alkynyl group having 2 to 30 carbon atoms, a silyl group having 3 to 18 carbon atoms, an acyl group having 2 to 19 carbon atoms, an aromatic hydrocarbon group having 6 to 50 carbon atoms, or an aromatic heterocyclic group having 3 to 50 carbon atoms and free of a fused heterocycle having 4 or more rings, X's each independently represent $C(R)_2$, oxygen, sulfur, or selenium, R's each independently represent hydrogen, an alkyl group having 1 to 30 carbon atoms, a cycloalkyl group having 3 to 30 carbon atoms, an alkenyl group having 2 to 30 carbon atoms, an alkynyl group having 2 to 30 carbon atoms, an aromatic hydrocarbon group having 6 to 30 carbon atoms, or an aromatic heterocyclic group having 3 to 30 carbon atoms and free of a fused heterocycle having 4 or more rings, m represents 1 to 4, n represents 0 to 3, and the total number of m and n is 2 to 4.

Of the compounds represented by the general formula (1), a nitrogen-containing aromatic compound represented by the formula (2) is given as a preferred compound.

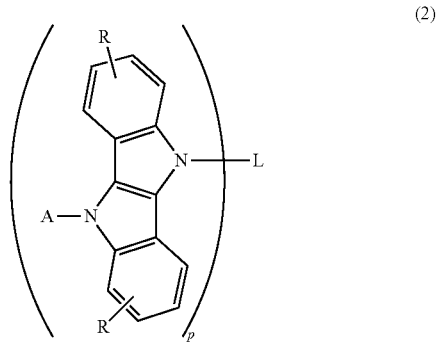

(2)

In the formula (2), L, A, and R's each have the same meaning as that in the general formula (1), and p represents an integer of 2 to 4.

Further, a nitrogen-containing aromatic compound in which p in the general formula (2) represents 2 or 3 is given as a preferred compound.

The organic layer which contains the nitrogen-containing aromatic compound represented by the general formula (1) preferably includes at least one layer selected from the group consisting of a light-emitting layer, a hole-transporting layer, and an electron-blocking layer.

The organic layer which contains the nitrogen-containing aromatic compound represented by the general formula (1) more preferably includes a light-emitting layer containing a phosphorescent light-emitting dopant.

BRIEF DESCRIPTION OF DRAWINGS

FIG. 1 is a sectional view illustrating an example of the structure of an organic EL device.

DESCRIPTION OF EMBODIMENTS

An organic electroluminescent device of the present invention contains a nitrogen-containing aromatic compound represented by the general formula (1) (hereinafter sometimes referred to as "compound represented by the general formula (1)" or "nitrogen-containing aromatic compound").

In each of the general formula (1) and the formula (2), L represents an n+m-valent bonding group. The bonding group is a group produced by removing n+m hydrogen atoms from an alkane having 1 to 30 carbon atoms, a cycloalkane having 3 to 30 carbon atoms, an aromatic hydrocarbon having 6 to 50 carbon atoms, an aromatic heterocyclic compound having 3 to 50 carbon atoms, a triarylamine having 9 to 30 carbon atoms, or a diarylsulfone having 6 to 24 carbon atoms. Here, the aromatic heterocyclic group is free of a fused heterocycle having 4 or more rings.

L preferably represents a group produced by removing n+m hydrogen atoms from an alkane having 1 to 10 carbon atoms, a cycloalkane having 3 to 11 carbon atoms, an aromatic hydrocarbon having 6 to 30 carbon atoms, an aromatic heterocyclic compound having 3 to 30 carbon atoms, a triarylamine having 9 to 22 carbon atoms, or a diarylsulfone having 6 to 20 carbon atoms. L more preferably represents a group produced by removing n+m hydrogen atoms from an alkane having 1 to 10 carbon atoms, a cycloalkane having 3 to 11 carbon atoms, an aromatic hydrocarbon having 6 to 30 carbon atoms, or an aromatic heterocyclic compound having 3 to 30 carbon atoms.

When L represents a group arising from the alkane having 1 to 30 carbon atoms, the number of carbon atoms of the group is preferably 1 to 10, more preferably 1 to 8. Specific examples of the alkane include methane, ethane, propane, butane, pentane, hexane, heptane, octane, nonane, and decane. Preferred examples thereof include methane, ethane, propane, butane, pentane, hexane, heptane, and octane. The group arising from the alkane may be linear or branched.

The group arising from the alkane may have a substituent, and when such group has a substituent, the substituent is a cycloalkyl group having 3 to 11 carbon atoms, an aromatic hydrocarbon group having 6 to 18 carbon atoms, or an aromatic heterocyclic group having 3 to 18 carbon atoms.

When the group arising from the alkane has a substituent, the total number of substituents is 1 to 10. The total number is preferably 1 to 6, more preferably 1 to 4. In addition, when the group has 2 or more substituents, the substituents may be identical to or different from each other.

When L represents a group arising from the cycloalkane having 3 to 30 carbon atoms, the number of carbon atoms of the group is preferably 3 to 11, more preferably 5 to 6. Specific examples of the cycloalkane include cyclopropane, cyclobutane, cyclopentane, cyclohexane, cycloheptane, cyclooctane, and decahydronaphthane. Preferred examples thereof include cyclopentane and cyclohexane.

The group arising from the cycloalkane may have a substituent, and when such group has a substituent, the substituent is an alkyl group having 1 to 10 carbon atoms, an aromatic hydrocarbon group having 6 to 18 carbon atoms, or an aromatic heterocyclic group having 3 to 18 carbon atoms.

When the group arising from the cycloalkane has a substituent, the total number of substituents is 1 to 10. The total number is preferably 1 to 6, more preferably 1 to 4. In addition, when the group has 2 or more substituents, the substituents may be identical to or different from each other.

When L represents a group arising from an aromatic hydrocarbon having 6 to 50 carbon atoms or an aromatic heterocyclic compound having 3 to 50 carbon atoms, the number of carbon atoms of the aromatic hydrocarbon is preferably 6 to 30, more preferably 6 to 18, and the number of carbon atoms of the aromatic heterocycle is preferably 3 to 30, more preferably 3 to 18. Here, the aromatic heterocyclic compound or an aromatic heterocyclic group arising therefrom is free of a fused heterocycle having 4 or more rings.

Specific examples of the aromatic hydrocarbon and the aromatic heterocyclic compound include benzene, pentalene, indene, naphthalene, azulene, heptalene, octalene, indacene, acenaphthylene, phenalene, phenanthrene, anthracene, trindene, fluoranthene, acephenanthrylene, aceanthrylene, triphenylene, pyrene, chrysene, tetraphene, tetracene, pleiadene, picene, perylene, pentaphene, pentacene, tetraphenylene, cholanthrylene, helicene, hexaphene, rubicene, coronene, trinaphthylene, heptaphene, pyranthrene, furan, benzofuran, isobenzofuran, xanthene, oxathrene, dibenzofuran, peri-xanthenoxanthene, thiophene, thioxanthene, thianthrene, phenoxathiin, thionaphthene, isothianaphtene, thiophthene, thiophanthrene, dibenzothiophene, pyrrole, pyrazole, tellurazole, selenazole, thiazole, isothiazole, oxazole, furazan, pyridine, pyrazine, pyrimidine, pyridazine, triazine, indolizine, indole, isoindole, indazole, purine, quinolizine, isoquinoline, carbazole, imidazole, naphthyridine, phthalazine, quinazoline, benzodiazepine, quinoxaline, cinnoline, quinoline, pteridine, phenanthridine, acridine, perimidine, phenanthroline, phenazine, carboline, phenotellurazine, phenoselenazine, phenothiazine, phenoxazine, anthyridine, benzothiazole, benzimidazole, benzoxazole, benzisoxazole, benzisothiazole, and an aromatic compound in which a plurality of such aromatic rings are linked to each other. Preferred examples thereof include benzene, naphthalene, anthracene, pyridine, pyrazine, pyrimidine, pyridazine, triazine, isoindole, indazole, purine, isoquinoline, imidazole, naphthyridine, phthalazine, quinazoline, benzodiazepine, quinoxaline, cinnoline, quinoline, pteridine, phenanthridine, acridine, perimidine, phenanthroline, phenazine, carboline, indole, carbazole, and an aromatic compound in which a plurality of such aromatic rings are linked to each other.

It should be noted that in the case of the group produced from an aromatic compound in which a plurality of aromatic rings are linked to each other, the number of the aromatic rings to be linked to each other is preferably 2 to 10, more preferably 2 to 7, and the aromatic rings to be linked to each other may be identical to or different from each other. In that case, the bonding position of L to be bonded to nitrogen is not limited, and L may be bonded to a ring at a terminal portion of linked aromatic rings or may be bonded to a ring at the central portion thereof. Here, the term "aromatic ring" is a generic term for an aromatic hydrocarbon ring and an aromatic heterocycle. In addition, when the linked aromatic rings include at least one heterocycle, the linked aromatic rings are included in the category of the aromatic heterocyclic group.

Here, the monovalent group produced by the linking of a plurality of aromatic rings is, for example, represented by any one of the following formulae. When L represents an n+m-valent bonding group, the group is understood to be a group produced by removing n+m−1 hydrogen atoms from any of $Ar_1$ to $Ar_6$ in the following formulae.

(11)

(12)

(13)

(In the formulae (11) to (13), $Ar_1$ to $Ar_6$ each represent a substituted or non-substituted aromatic ring.)

Specific examples of the group produced by the linking a plurality of aromatic rings include groups each produced by removing hydrogen from, for example, biphenyl, terphenyl, bipyridine, bipyrimidine, bitriazine, terpyridine, bistriazylbenzene, dicarbazolylbenzene, carbazolylbiphenyl, dicarbazolylbiphenyl, phenylterphenyl, carbazolylterphenyl, binaphthalene, phenylpyridine, phenylcarbazole, diphenylcarbazole, diphenylpyridine, phenylpyrimidine, diphenylpyrimidine, phenyltriazine, diphenyltriazine, phenylnaphthalene, or diphenylnaphthalene.

Here, the aromatic heterocyclic compound or aromatic heterocyclic group arising therefrom free of a fused heterocycle having 4 or more rings means a monocyclic aromatic heterocyclic compound or group, or a fused aromatic heterocyclic compound or group having 2 to 3 rings, and the aromatic heterocyclic compound or group may have a substituent. It should be noted that when the aromatic heterocyclic group is, for example, such a group produced by the linking of a plurality of aromatic rings as represented by the formula (11), a monovalent or divalent aromatic heterocyclic group in the aromatic group is not a fused ring group having 4 or more rings.

The aromatic hydrocarbon group or the aromatic heterocyclic group may have a substituent, and when any such group has a substituent, the substituent is an alkyl group having 1 to 4 carbon atoms, a cycloalkyl group having 3 to 6 carbon atoms, an alkoxy group having 1 to 2 carbon atoms, an acetyl group, a secondary amino group having 6 to 18 carbon atoms, a secondary phosphanyl group having 6 to 18 carbon atoms, or a silyl group having 3 to 18 carbon atoms. The substituent is preferably an alkyl group having 1 to 4 carbon atoms, a cycloalkyl group having 3 to 6 carbon atoms, or a secondary amino group having 6 to 15 carbon atoms.

When L represents an aromatic hydrocarbon group or an aromatic heterocyclic group, and the group has a substituent, the total number of substituents is 1 to 10. The number is preferably 1 to 6, more preferably 1 to 4. In addition, when the group has two or more substituents, the substituents may be identical to or different from each other.

In the description, in the calculation of the number of carbon atoms, when the group has a substituent, the number of carbon atoms of the substituent is also included.

When L represents a group arising from the triarylamine having 9 to 30 carbon atoms, the number of carbon atoms of the group is preferably 9 to 24, more preferably 9 to 18. The group arising from the triarylamine is an n+m-valent group produced by removing n+m hydrogen atoms from any Ar of a triarylamine represented by the following formula (5).

(3)

In the formula (3), three Ar's each represent a monovalent to (m+n+1)-valent aromatic group, and three Ar's may be identical to or different from one another and may be different from one another in valence. Ar represents an aromatic hydrocarbon group having 6 to 18 carbon atoms or an aromatic heterocyclic group having 3 to 18 carbon atoms. Ar preferably represents a phenyl group, a naphthyl group, a pyridyl group, a quinolyl group, or a carbazolyl group, and more preferably represents a phenyl group. Here, the aromatic heterocyclic group is free of a fused heterocycle having 4 or more rings.

Ar may have a substituent, and when Ar has a substituent, the substituent is an alkyl group having 1 to 4 carbon atoms, a cycloalkyl group having 3 to 6 carbon atoms, an alkoxy group having 1 to 2 carbon atoms, or an acetyl group.

When L represents a group arising from the diarylsulfone having 6 to 24 carbon atoms, the number of carbon atoms of the group is preferably 6 to 20, more preferably 6 to 18. The group arising from the diarylsulfone is an n+m-valent group produced by removing n+m hydrogen atoms from any Ar of a diarylsulfone represented by the following formula (3).

(4)

In the formula (4), Ar's each have the same meaning as that of each Ar in the formula (3).

In the general formula (1), X's each independently represent $C(R)_2$, oxygen, sulfur, or selenium. It is preferred that X's each represent oxygen or sulfur.

In the general formula (1), A's each independently represent an alkyl group having 1 to 30 carbon atoms, a cycloalkyl group having 3 to 30 carbon atoms, an alkenyl group having 2 to 30 carbon atoms, an alkynyl group having 2 to 30 carbon atoms, a silyl group having 3 to 18 carbon atoms, an acyl group having 2 to 19 carbon atoms, an aromatic hydrocarbon group having 6 to 50 carbon atoms, or an aromatic heterocyclic group having 3 to 50 carbon atoms. It is preferred that A's each represent an alkyl group having 1 to 10 carbon atoms, a cycloalkyl group having 3 to 11 carbon atoms, an aromatic hydrocarbon group having 6 to 30 carbon atoms, or an aromatic heterocyclic group having 3 to 30 carbon atoms. Here, the aromatic heterocyclic group is free of a fused heterocycle having 4 or more rings.

Specific examples of the case where A represents an alkyl group or a cycloalkyl group are identical to those of the alkyl or cycloalkyl group constituting L except that the former group is a monovalent group. In addition, description in the case of L holds true for the case where such alkyl or cycloalkyl group has a substituent.

When A represents an alkenyl group having 2 to 30 carbon atoms or an alkynyl group having 2 to 30 carbon atoms, the number of carbon atoms of the group is preferably 2 to 20, more preferably 2 to 10. Specific examples of the alkenyl group and the alkynyl group include an ethylenyl group, a propylenyl group, a butenyl group, a pentenyl group, a hexenyl group, a heptenyl group, an octenyl group, an acetylenyl group, a propynyl group, a butynyl group, and a pentynyl group. Preferred examples thereof include an ethylenyl group, a propylenyl group, a butenyl group, an acetylenyl group, and a propynyl group. The alkenyl group and the alkynyl group may be linear or branched.

The alkenyl group or the alkynyl group may have a substituent, and when any such group has a substituent, the substituent is a cycloalkyl group having 3 to 11 carbon atoms, an aromatic hydrocarbon group having 6 to 18 carbon atoms, or an aromatic heterocyclic group having 3 to 18 carbon atoms.

When A represents a silyl group having 3 to 18 carbon atoms, the number of carbon atoms of the group is preferably 3 to 12, more preferably 3 to 9. The silyl group is represented by $-SiZ_3$, Z's each represent hydrogen or a hydrocarbon group, and all Z's each preferably represent a hydrocarbon group. Preferred examples of the hydrocarbon group include an alkyl group and a phenyl group. Three Z's may be identical to or different from one another and the number of carbon atoms is calculated as the sum of their carbon atoms. The silyl group is preferably an alkyl silyl group.

Specific examples of the alkyl silyl group include a trimethylsilyl group, a triethylsilyl group, a tri(n-propyl)silyl group, a tri(n-butyl)silyl group, a trivinylsilyl group, a trimethoxysilyl group, a triethoxysilyl group, a tri(isopropoxy) silyl group, a tri(n-butoxy)silyl group, a tri(s-butoxy)silyl group, a tri(t-butoxy)silyl group, a triisopropylsilyl group, a tricyclohexylsilyl group, a tri(s-butyl)silyl group, a triethynylsilyl group, a triallylsilyl group, a tripropargylsilyl group, a triphenylsilyl group, a t-butyldimethylsilyl group, a t-butyldiethylsilyl group, an isopropyldimethylsilyl group, a cyclohexyldimethylsilyl group, a dimethylphenylsilyl group, a diethylphenylsilyl group, an isopropyldimethylsilyl group, an isopropyldiethylsilyl group, a methyldiisopropylsilyl group, an ethyldiisopropylsilyl group, a cyclopentyldimethylsilyl group, and a cyclohexylmethylsilyl group. Of those, preferred is a trimethylsilyl group, a triisopropylsilyl group, a t-butyldimethylsilyl group, or a triphenylsilyl group.

When A represents an acyl group having 2 to 19 carbon atoms, the number of carbon atoms of the group is preferably 6 to 19, more preferably 7 to 13. The acyl group is preferably a monovalent group represented by the following formula (5).

(5)

In the formula (5), Ar represents an aromatic hydrocarbon group having 6 to 18 carbon atoms, or an aromatic heterocyclic group having 3 to 18 carbon atoms and free of a fused heterocycle having 4 or more rings. Ar preferably represents a phenyl group, a naphthyl group, a pyridyl group, a quinolyl group, or a carbazolyl group, and more preferably represents a phenyl group.

Ar may have a substituent, and when Ar has a substituent, the substituent is an alkyl group having 1 to 4 carbon atoms, a cycloalkyl group having 3 to 6 carbon atoms, an alkoxy group having 1 to 2 carbon atoms, or an acetyl group.

When A represents an aromatic hydrocarbon group having 6 to 50 carbon atoms or an aromatic heterocyclic group having 3 to 50 carbon atoms, the number of carbon atoms of the aromatic hydrocarbon group is preferably 6 to 30, more preferably 6 to 18, and the number of carbon atoms of the aromatic heterocyclic group is preferably 3 to 30, more preferably 3 to 18. Here, the aromatic heterocyclic group is free of a fused heterocycle having 4 or more rings.

Specific examples of the case where A represents a group selected from an aromatic hydrocarbon group and an aromatic heterocyclic group are identical to those of the aromatic hydrocarbon group or aromatic heterocyclic group constituting L except that the former group is monovalent.

In each of the general formula (1) and the formula (2), R's each independently represent hydrogen, an alkyl group having 1 to 30 carbon atoms, a cycloalkyl group having 3 to 30 carbon atoms, an alkenyl group having 2 to 30 carbon atoms, an alkynyl group having 2 to 30 carbon atoms, an aromatic hydrocarbon group having 6 to 30 carbon atoms, or an aromatic heterocyclic group having 3 to 30 carbon atoms. R's each preferably represent hydrogen, an alkyl group having 1 to 10 carbon atoms, a cycloalkyl group having 3 to 11 carbon atoms, an aromatic hydrocarbon group having 6 to 18 carbon atoms, or an aromatic heterocyclic group having 3 to 18 carbon atoms. Here, the aromatic heterocyclic group is free of a fused heterocycle having 4 or more rings. In addition, R's in the case where X represents $C(R)_2$ each have the same meaning as the foregoing.

Specific examples of the alkyl group or the cycloalkyl group are identical to those of the alkyl or cycloalkyl group constituting L except that the former group is monovalent. In addition, description in the case of L holds true for the case where such alkyl or cycloalkyl group has a substituent.

Specific examples of the alkenyl group or the alkynyl group are identical to those of the alkenyl group or alkynyl group described for A. In addition, description in the case of A holds true for the case where such alkenyl group or alkynyl group has a substituent.

Specific examples of the aromatic hydrocarbon group or the aromatic heterocyclic group are identical to those of the aromatic hydrocarbon group or aromatic heterocyclic group constituting L except for a difference in total number of carbon atoms. In addition, description in the case of L holds true for the case where such aromatic hydrocarbon group or aromatic heterocyclic group has a substituent.

In the general formula (1), m represents an integer of 1 to 4. m preferably represents 2 or 3 and m more preferably represents 2. n represents an integer of 0 to 3. n preferably represents 0 or 1 and n more preferably represents 0.

In the general formula (1), m+n is 2 to 4. m+n is preferably 2 or 3, more preferably 2.

In the general formula (1) and the formula (2), common symbols have the same meaning.

In the formula (2), p represents an integer of 2 to 4. p preferably represents 2 or 3 and more preferably represents 2.

The nitrogen-containing aromatic compound of the present invention can be synthesized from an indole derivative as a starting material by employing a known approach after selecting raw materials in accordance with the structure of the target compound.

For example, an indolo[3,2-b]indole skeleton can be synthesized by the following reaction formula with reference to a synthesis example described in each of J. Org. Chem., 2009, 4242-4245, Journal of Medicinal Chemistry, 2003, 2436-2445, and J. Am. Chem. Soc., 1994, 8152-8161.

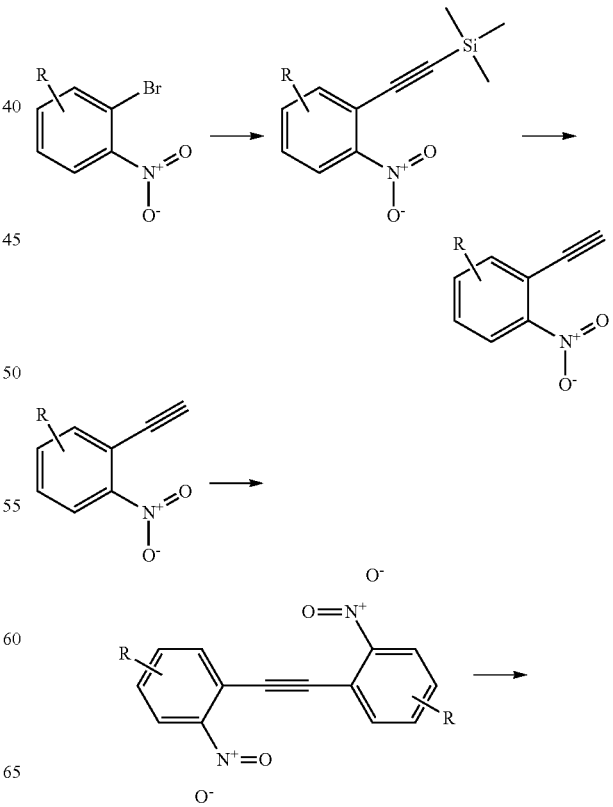

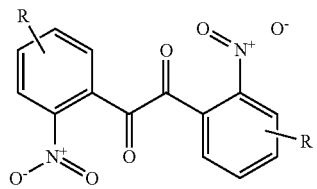

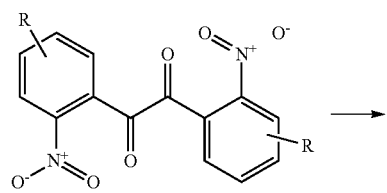

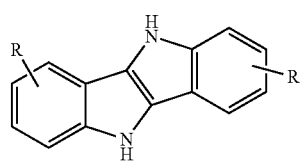

In addition, out of skeletons each having a [3,2-b]fusion mode, a benzofuro[3,2-b]indole skeleton in which X represents oxygen can be synthesized by the following reaction formula with reference to a synthesis example described in each of Heterocycles, 1990, vol. 31, 1951-1958 and Journal of Chemical Research, 1988, 272-273.

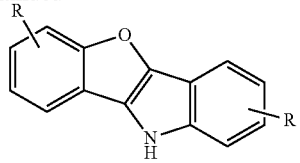

In addition, out of skeletons each having a [3,2-b]fusion mode, a benzothieno[3,2-b]indole skeleton in which X represents sulfur can be synthesized by the following reaction formula with reference to a synthesis example described in Tetrahedron, 2003, vol. 59, 3737-3744.

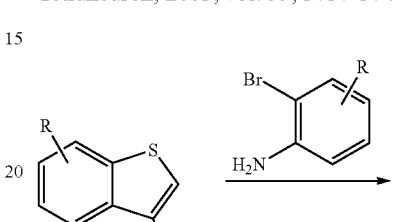

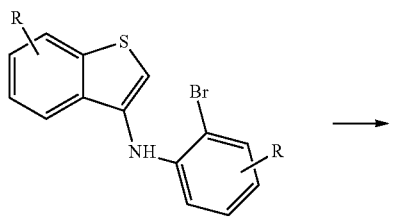

The nitrogen-containing aromatic compound represented by the general formula (1) can be synthesized by substituting hydrogen on nitrogen of each of the various compounds obtained by the foregoing reaction formulae with the corresponding linking group or substituent through a coupling reaction such as the Ullmann reaction.

Specific examples of the nitrogen-containing aromatic compound represented by the general formula (1) are shown below. However, a material to be used for an organic electroluminescent device of the present invention is not limited thereto.

(1-1)

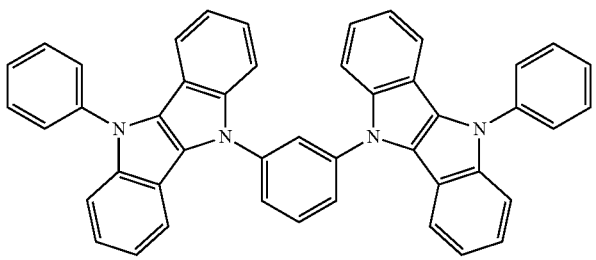

(1-2)

(1-3)

(1-4)

(1-5)

(1-6)

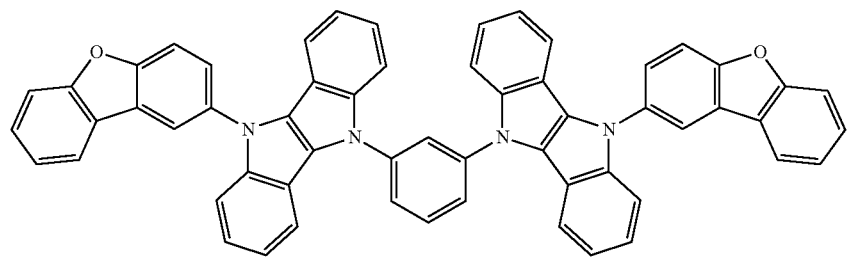
(1-7)
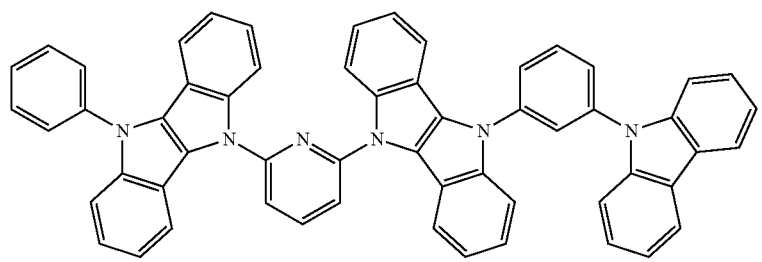
(1-8)
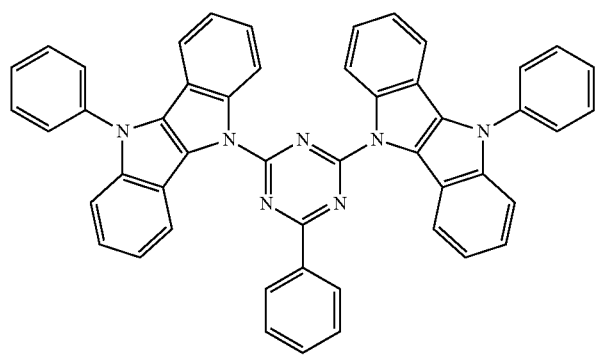
(1-9)
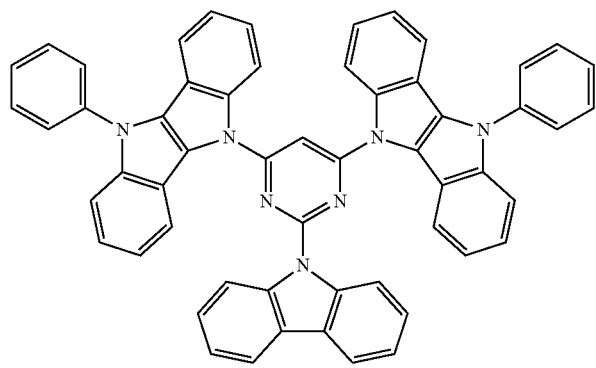
(1-10)

(1-11)
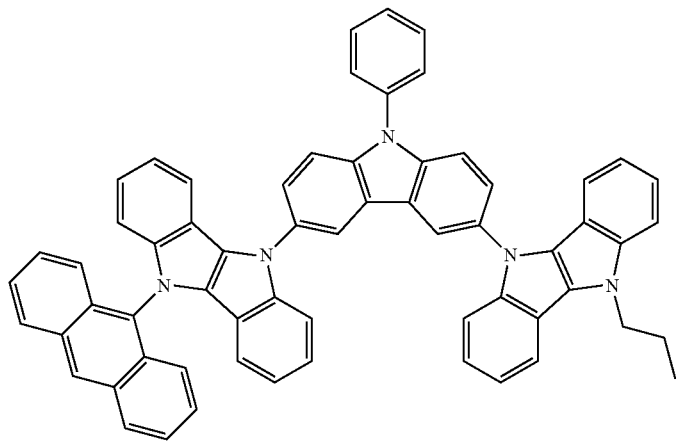
(1-12)
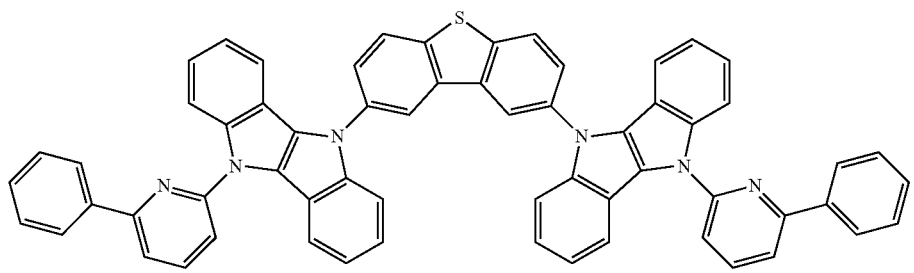
(1-13)
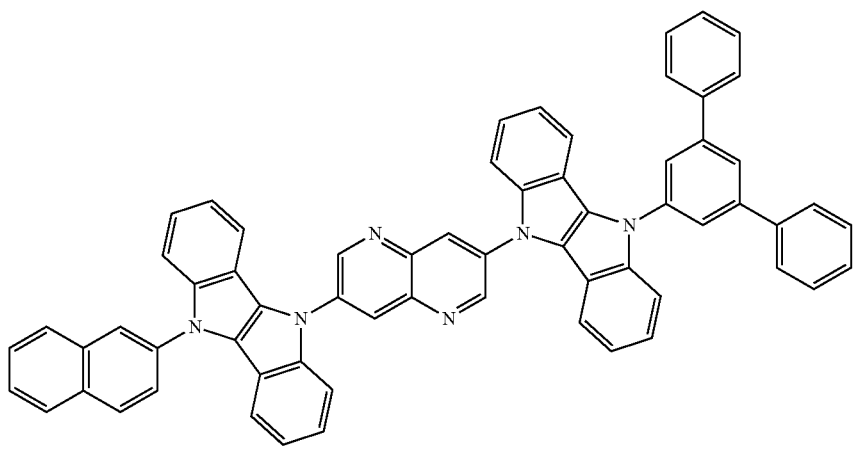
(1-14)
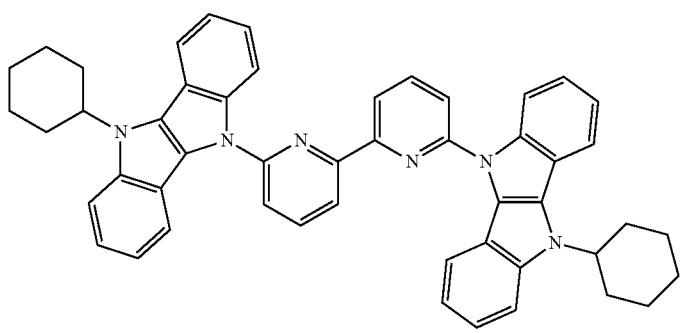

(1-15)
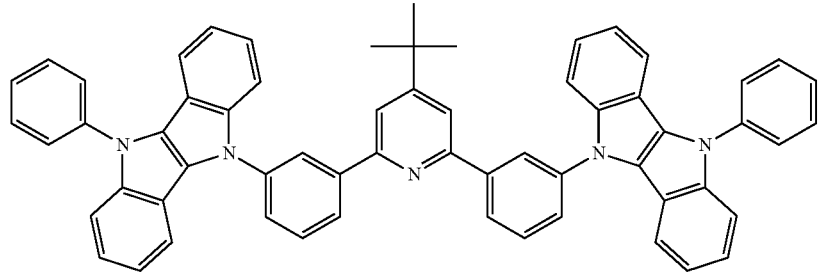
(1-16)
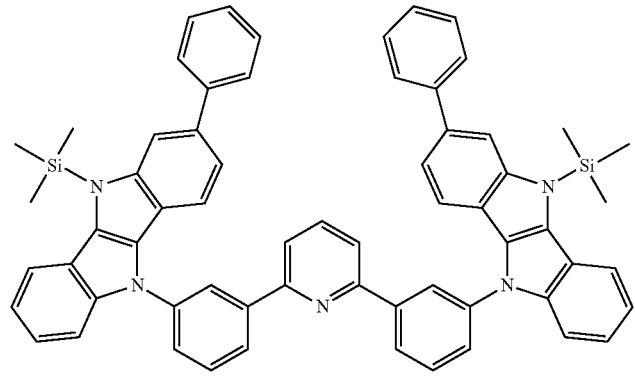
(1-17)
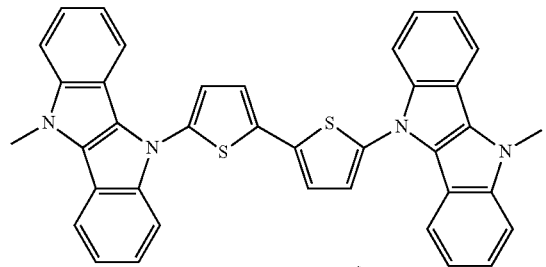
(1-18)
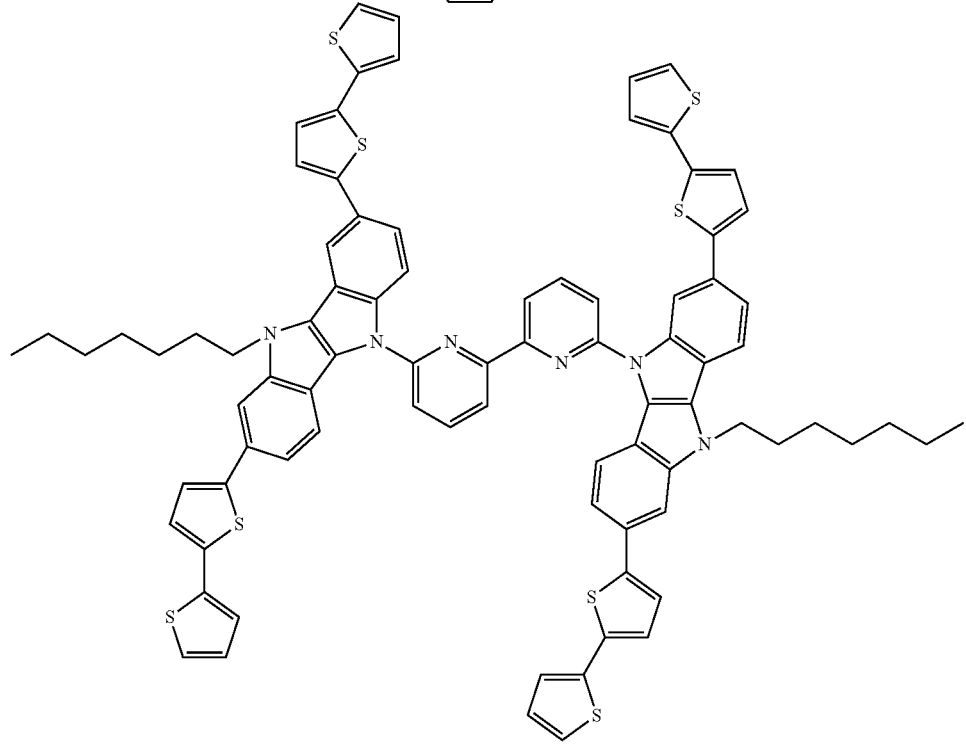

(1-19)
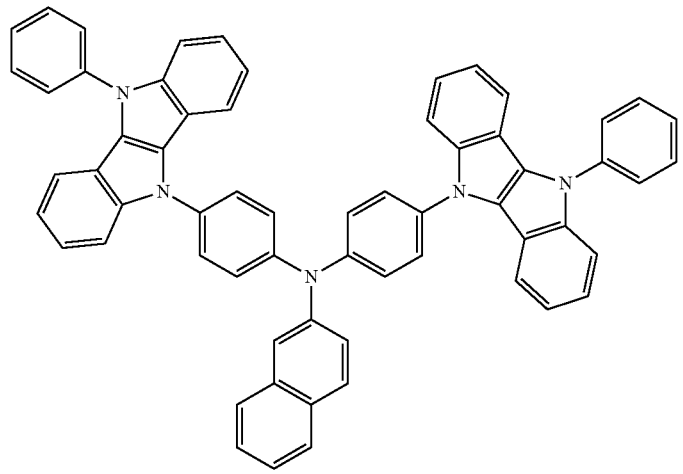
(1-20)
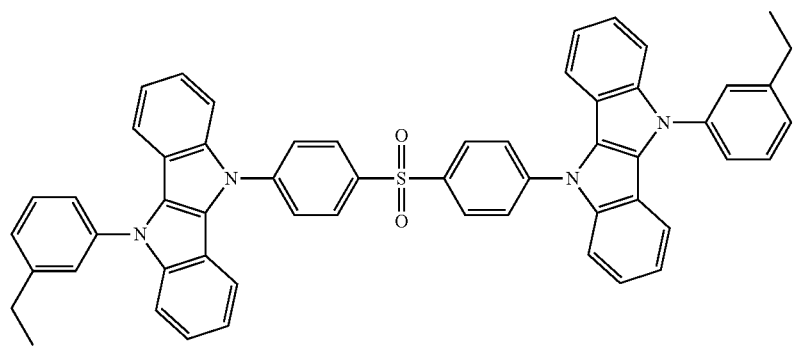
(1-21)
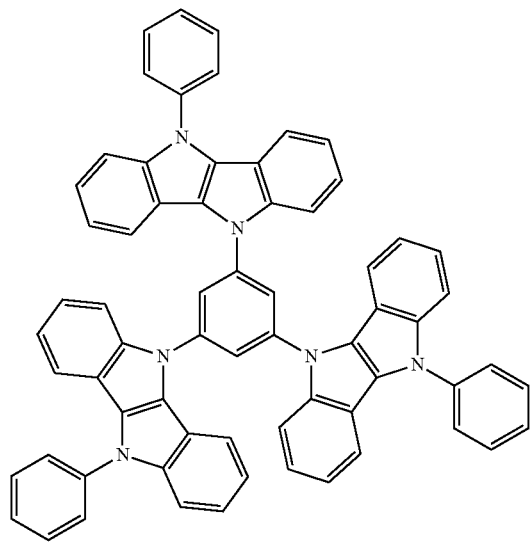

-continued
(1-22)
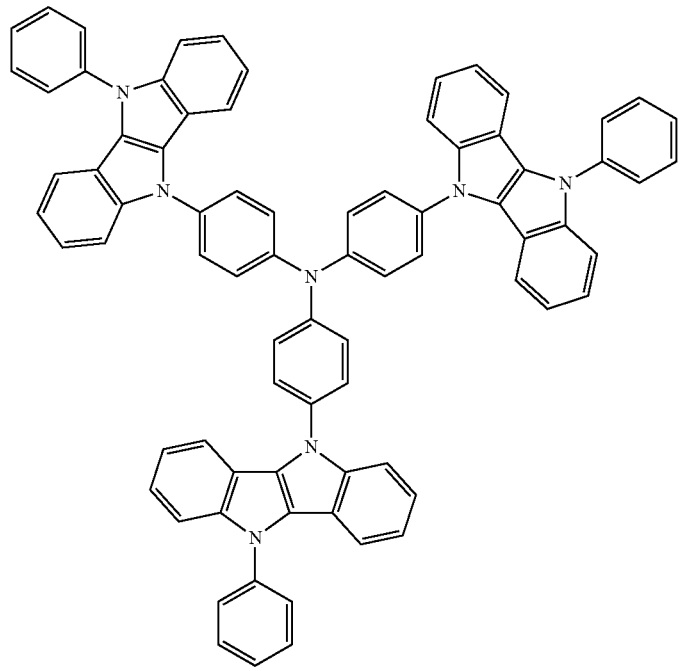
(1-23)
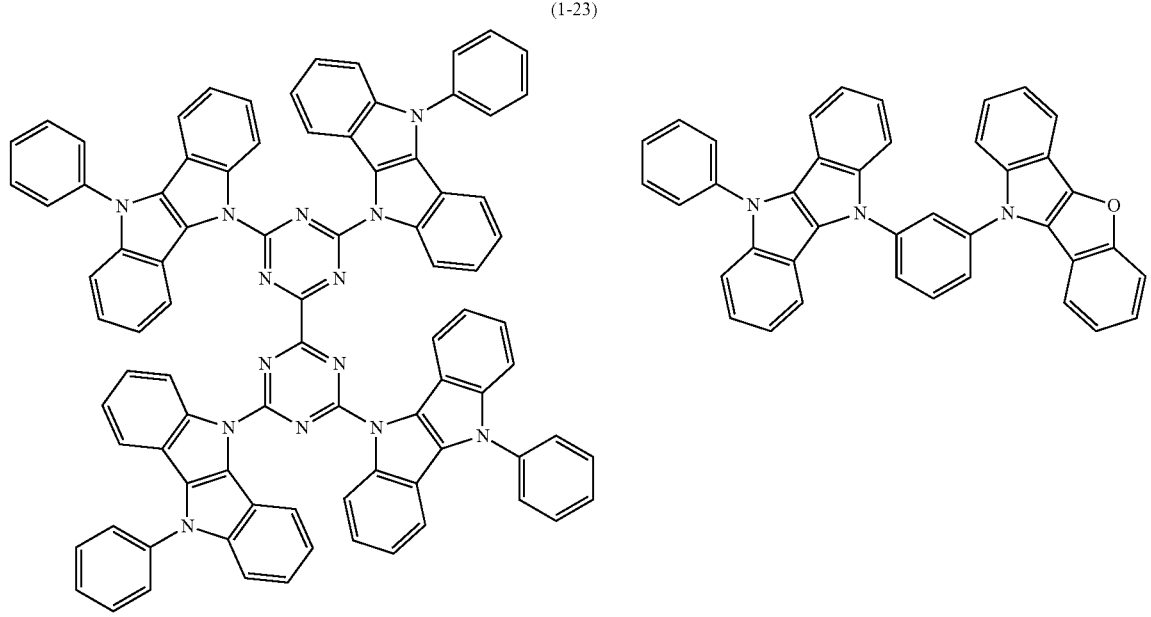
(2-1)
(2-2)
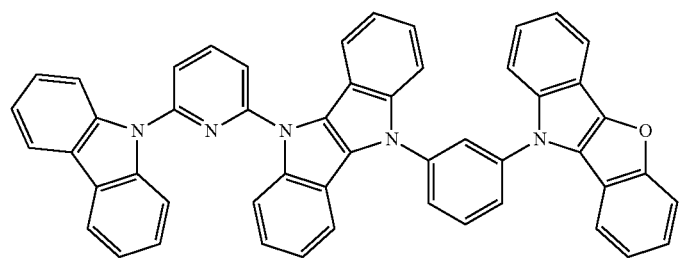

(2-3)
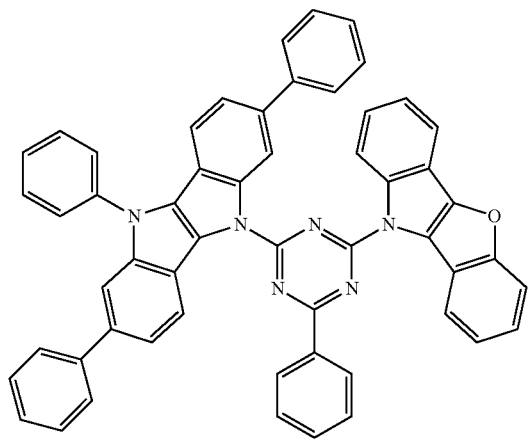
(2-4)
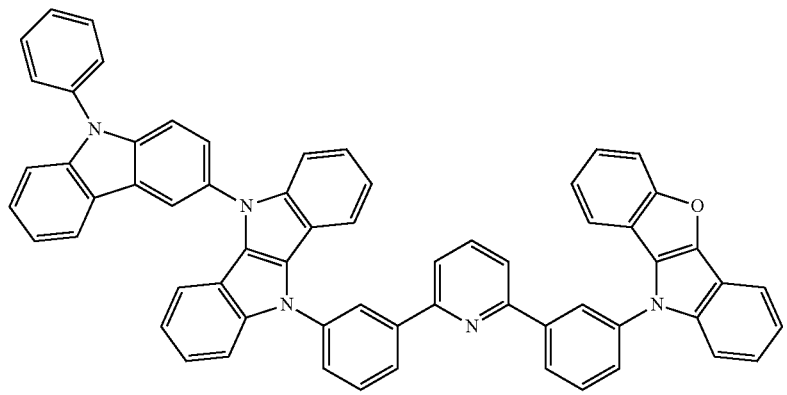
(2-5)
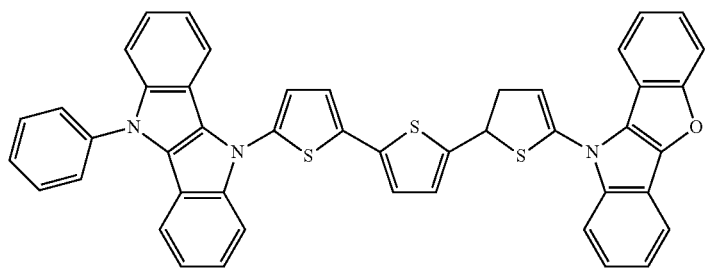
(2-6)
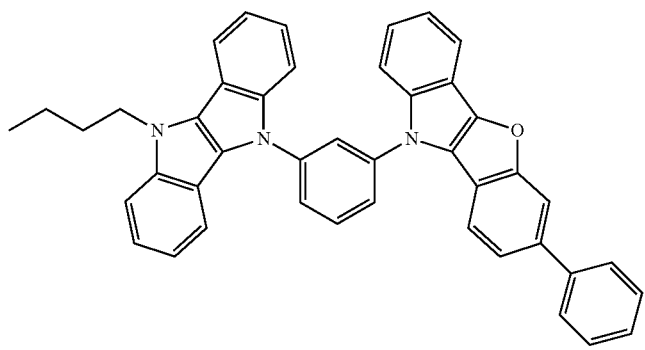

-continued
(2-7)
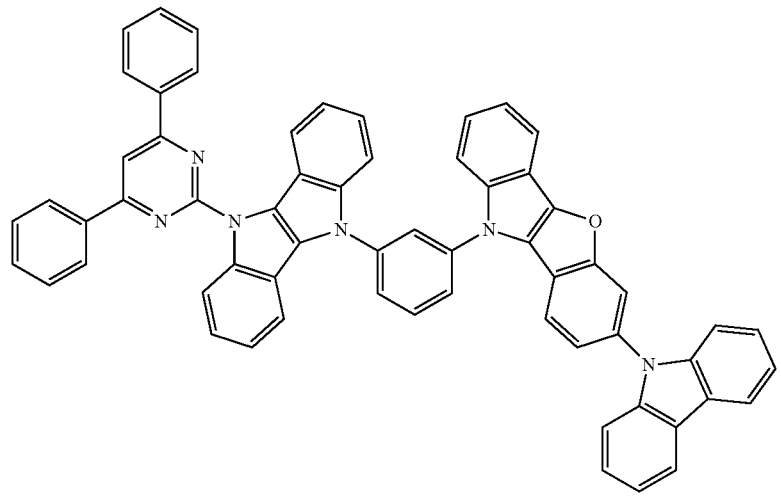
(2-8)
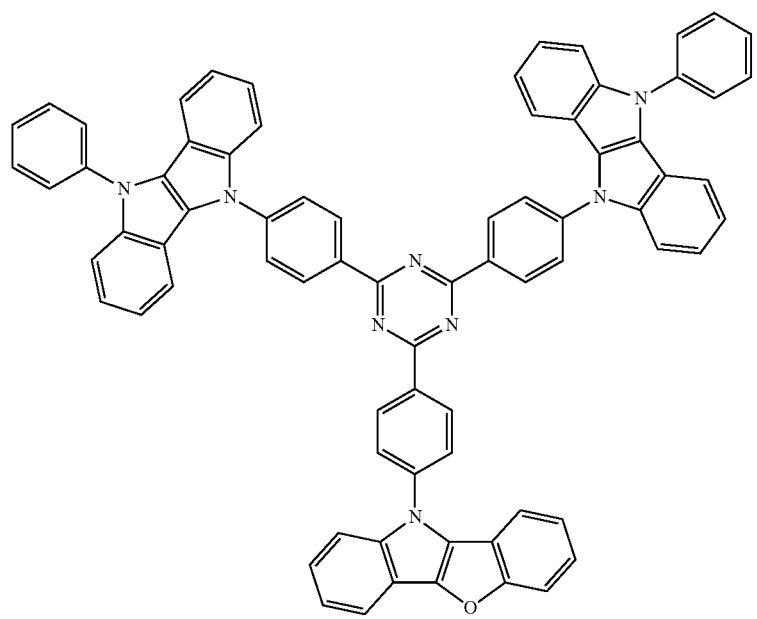
(2-9)
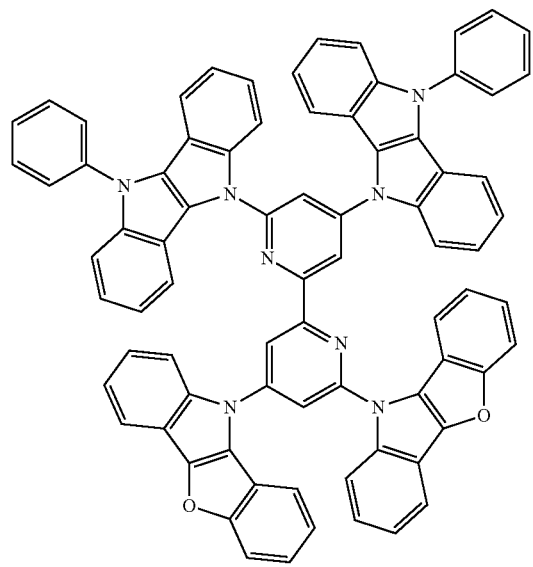

(2-10)
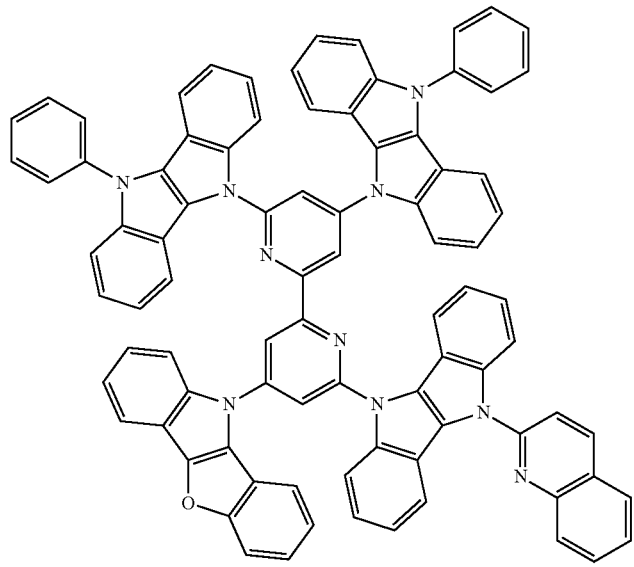
(3-1)
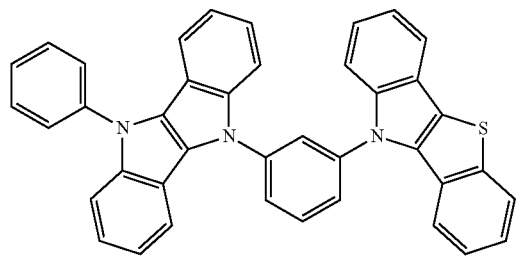
(3-2)
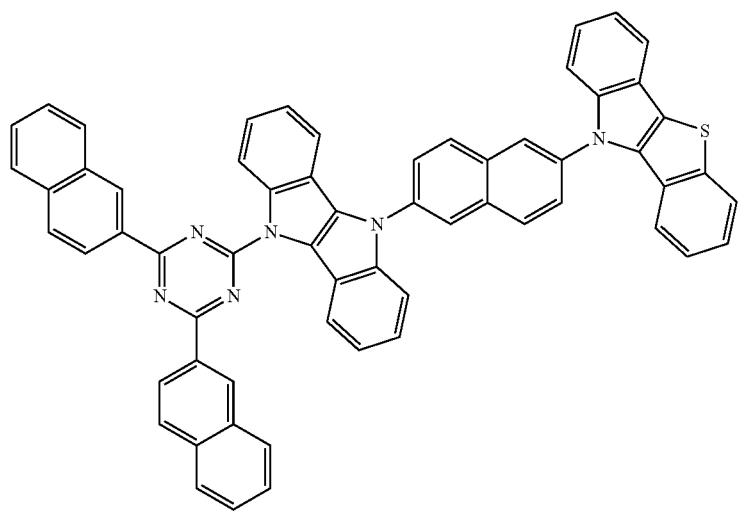

-continued
(3-3)
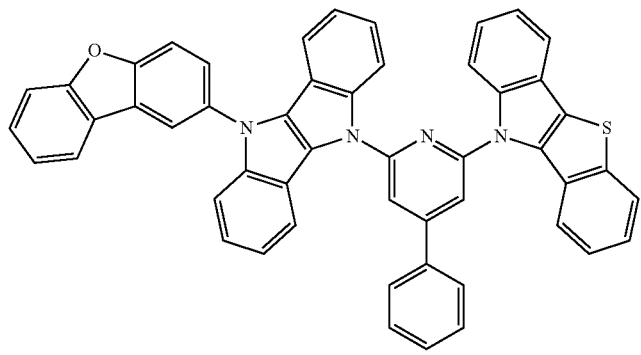
(3-4)
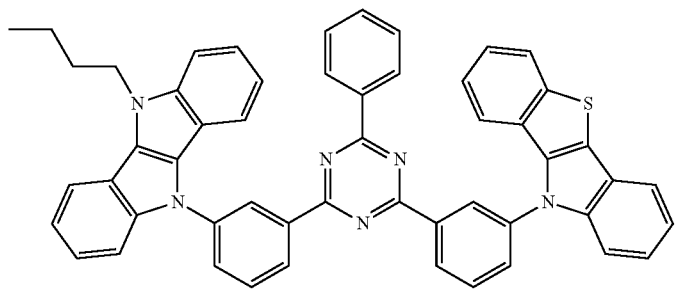
(3-5)
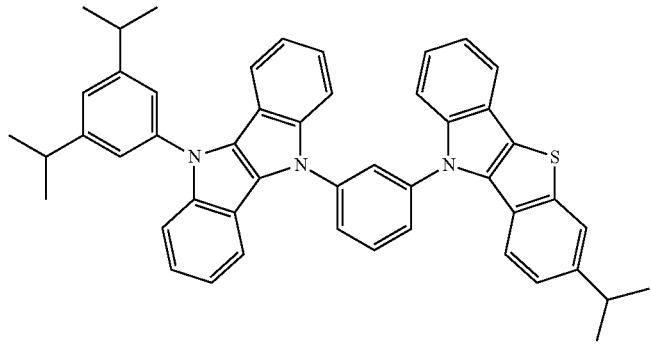
(3-6)
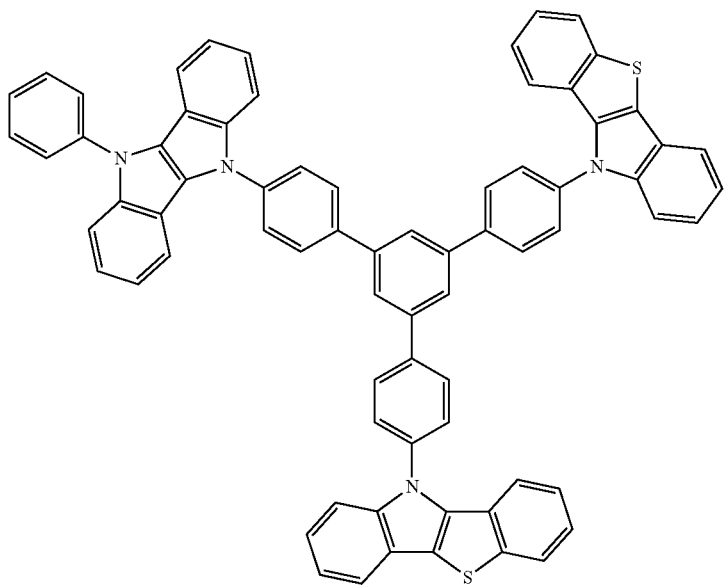

(3-7)
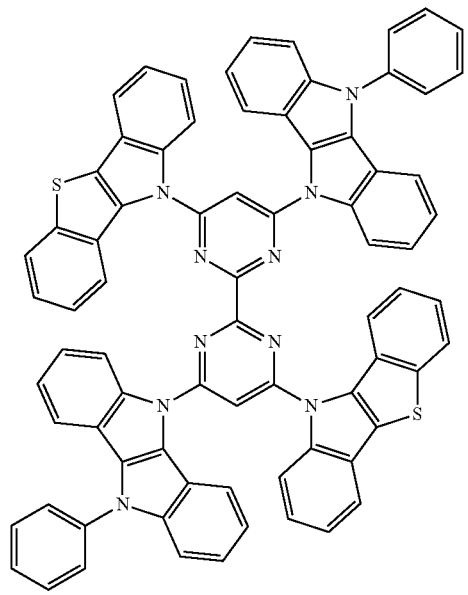
(4-1)
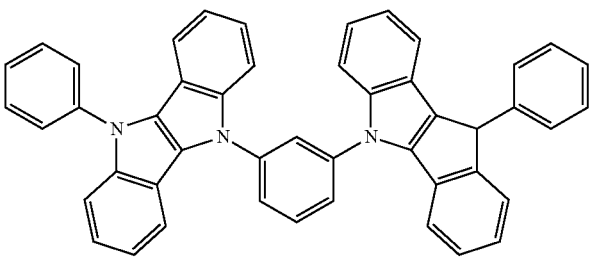
(4-2)
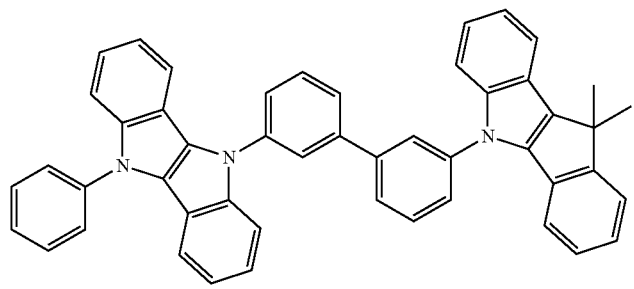
(4-3)
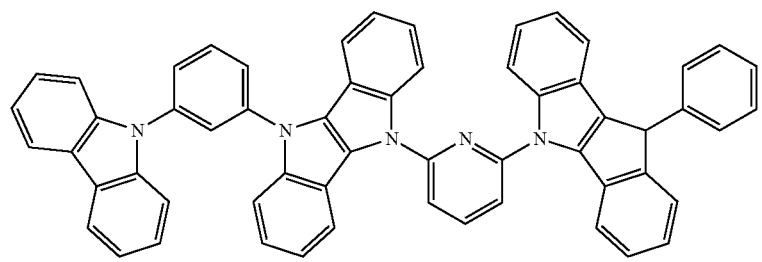
(4-4)
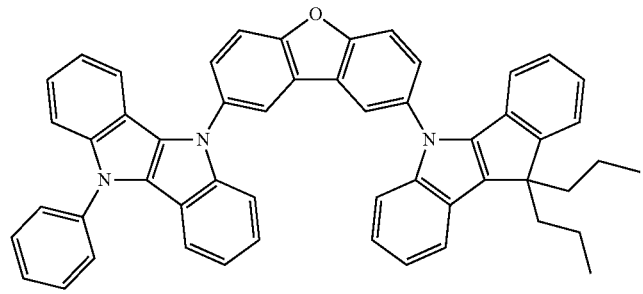

-continued

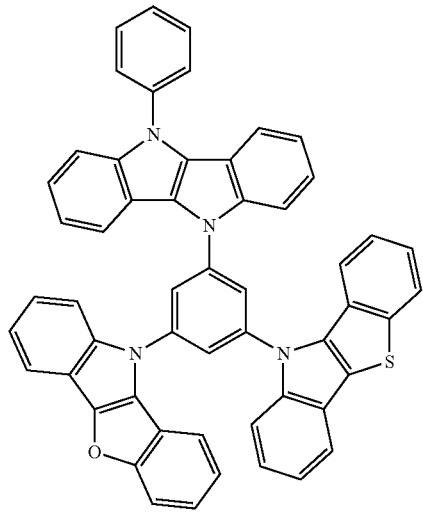
(5-1)

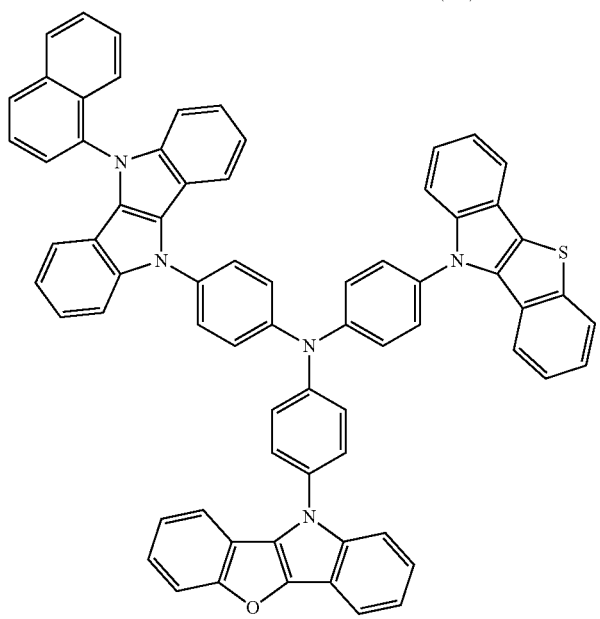
(5-2)

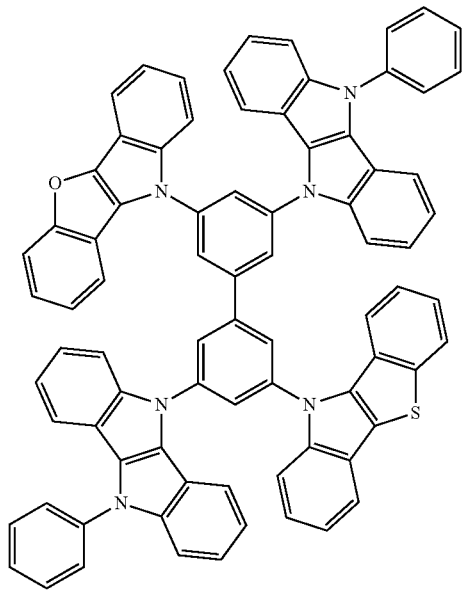
(5-3)

When the nitrogen-containing aromatic compound represented by the general formula (1) is contained in at least one of a plurality of organic layers of an organic EL device formed by laminating an anode, the plurality of organic layers, and a cathode on a substrate, an excellent organic electroluminescent device is provided. A light-emitting layer, a hole-transporting layer, and an electron-blocking layer are each preferred as the organic layer in which the nitrogen-containing aromatic compound is contained. It is more preferred that the nitrogen-containing aromatic compound be contained as a host material in a light-emitting layer containing a phosphorescent light-emitting dopant.

Next, the organic EL device of the present invention is described.

The organic EL device of the present invention has organic layers including at least one light-emitting layer between an anode and a cathode laminated on a substrate. In addition, at least one of the organic layers contains the compound represented by the general formula (1) of the present invention. The compound represented by the general formula (1) is advantageously contained in each of the light-emitting layer, a hole-transporting layer, and an electron-blocking layer. Further, the compound represented by the general formula (1) is more advantageously contained in the light-emitting layer together with a phosphorescent light-emitting dopant.

Next, the structure of the organic EL device of the present invention is described with reference to the drawings. However, the structure of the organic EL device of the present invention is by no means limited to one illustrated in the drawings.

FIG. 1 is a sectional view illustrating a structural example of a general organic EL device used in the present invention. Reference numeral 1 represents a substrate, reference numeral 2 represents an anode, reference numeral 3 represents a hole-injecting layer, reference numeral 4 represents a hole-transporting layer, reference numeral 5 represents a light-emitting layer, reference numeral 6 represents an electron-transporting layer, and reference numeral 7 represents a cathode. The organic EL device of the present invention may have an exciton-blocking layer adjacent to the light-emitting layer, or may have an electron-blocking layer between the light-emitting layer and the hole-injecting layer. The exciton-blocking layer may be inserted on any of the anode side and the cathode side of the light-emitting layer, and may also be inserted simultaneously on both sides. The organic EL device of the present invention has the substrate, the anode, the light-emitting layer, and the cathode as its essential layers. The organic EL device of the present invention preferably has a hole-injecting/transporting layer and an electron-injecting/transporting layer in addition to the essential layers, and more preferably has a hole-blocking layer between the light-emitting layer and the electron-injecting/transporting layer. It should be noted that the hole-injecting/transporting layer means any one or both of the hole-injecting layer and the hole-transporting layer, and that the electron-injecting/transporting layer means any one or both of an electron-injecting layer and the electron-transporting layer.

It should be noted that it is possible to adopt a reverse structure compared with FIG. 1, that is, the reverse structure being formed by laminating the layers on the substrate 1 in the order of the cathode 7, the electron-transporting layer 6, the light-emitting layer 5, the hole-transporting layer 4, and the anode 2. In this case as well, some layers may be added or eliminated if necessary.

—Substrate—

The organic EL device of the present invention is preferably supported by a substrate. The substrate is not particularly limited, and any substrate that has long been conventionally used for an organic EL device may be used. For example, a substrate made of glass, a transparent plastic, quartz, or the like may be used.

—Anode—

Preferably used as the anode in the organic EL device is an anode formed by using, as an electrode substance, any of a metal, an alloy, an electrically conductive compound, and a mixture thereof, all of which have a large work function (4 eV or more). Specific examples of such electrode substance include metals such as Au and conductive transparent materials such as CuI, indium tin oxide (ITO), $SnO_2$, and ZnO. Further, it may be possible to use a material such as IDIXO ($In_2O_3$—ZnO), which may be used for manufacturing an amorphous, transparent conductive film. In order to produce the anode, it may be possible to form any of those electrode substances into a thin film by using a method such as vapor deposition or sputtering and form a pattern having a desired design thereon by photolithography. Alternatively, in the case of not requiring high pattern accuracy (about 100 μm or more), a pattern may be formed via a mask having a desired shape when any of the above-mentioned electrode substances is subjected to vapor deposition or sputtering. Alternatively, when a coatable substance such as an organic conductive compound is used, it is also possible to use a wet film-forming method such as a printing method or a coating method. When luminescence is taken out from the anode, the transmittance of the anode is desirably controlled to more than 10%. Further, the sheet resistance as the anode is preferably several hundred Ω/□ or less. Further, the thickness of the resultant film is, depending on the material used, selected from usually the range of 10 to 1,000 nm, preferably the range of 10 to 200 nm.

—Cathode—

On the other hand, used as the cathode is a cathode formed by using, as an electrode substance, any of a metal (referred to as electron-injecting metal), an alloy, an electrically conductive compound, and a mixture thereof, all of which have a small work function (4 eV or less). Specific examples of such electrode substance include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. Of those, for example, a mixture of an electron-injecting metal and a second metal as a stable metal having a larger work function value than the former metal, such as a magnesium/silver mixture, a magnesium/aluminum mixture, a magnesium/indium mixture, an aluminum/aluminum oxide ($Al_2O_3$) mixture, or a lithium/aluminum mixture, or aluminum is suitable from the viewpoints of electron-injecting property and durability against oxidation or the like. The cathode may be produced by forming any of those electrode substances into a thin film by using a method such as vapor deposition or sputtering. Further, the sheet resistance as the cathode is preferably several hundred Ω/□ or less, and the thickness of the resultant film is selected from usually the range of 10 nm to 5 μm, preferably the range of 50 to 200 nm. It should be noted that, in order for luminescence produced to pass through, any one of the anode and cathode of the organic EL device is preferably transparent or semi-transparent, because the light emission luminance improves.

Further, after any of the above-mentioned metals is formed into a film having a thickness of 1 to 20 nm as a cathode, any of the conductive transparent materials mentioned in the description of the anode is formed into a film on the cathode, thereby being able to produce a transparent or semi-transparent cathode. Then, by applying this, it is possible to produce a device in which both the anode and cathode have transparency.

—Light-Emitting Layer—

The light-emitting layer, which may be any one of a fluorescent light-emitting layer and a phosphorescent light-emitting layer, is preferably the phosphorescent light-emitting layer.

When the light-emitting layer is the fluorescent light-emitting layer, at least one kind of fluorescent light-emitting material may be used alone as a fluorescent light-emitting material, but it is preferred that the fluorescent light-emitting material be used as a fluorescent light-emitting dopant and a host material be incorporated.

Although the compound represented by the general formula (1) can be used as the fluorescent light-emitting material in the light-emitting layer, fluorescent light-emitting materials are known to the public by many patent literatures and the like and hence the fluorescent light-emitting material can be selected therefrom. Examples thereof include: a benzoxazole derivative, a benzimidazole derivative, a benzothiazole derivative, a styrylbenzene derivative, a polyphenyl derivative, a diphenylbutadiene derivative, a tetraphenylbutadiene derivative, a naphthalimide derivative, a coumarin derivative, a fused aromatic compound, a perinone derivative, an oxadiazole derivative, an oxazine derivative, an aldazine derivative, apyrrolidine derivative, a cyclopentadiene derivative, a bisstyrylanthracene derivative, a quinacridone derivative, a pyrrolopyridine derivative, a thiadiazolopyridine derivative, a cyclopentadiene derivative, a styrylamine derivative, a diketopyrrolopyrrole derivative, and an aromatic dimethylidyne compound; various metal complexes exemplified by a metal complex of an 8-quinolinol derivative and a metal complex, rare earth metal complex, or transition metal complex of a pyrromethene derivative; polymer compounds such as a polythiophene, a polyphenylene, and a polyphenylenevinylene; and an organic silane derivative. Preferred examples thereof include a fused aromatic compound, a styryl compound, a diketopyrrolopyrrole compound, an oxazine compound, and a metal complex, transition metal complex, or lanthanoid complex of pyrromethene. More preferable examples include naphthacene, pyrene, chrysene, triphenylene, benzo[c]phenanthrene, benzo[a]anthracene, pentacene, perylene, fluoranthene, acenaphthofluoranthene, dibenzo[a,j]anthracene, dibenzo[a,h]anthracene, benzo[a]naphthacene, hexacene, anthanthrene, naphtho[2,1-f]isoquinoline, α-naphthophenanthridine, phenanthroxazole, quinolino[6,5-f]quinoline, andbenzothiophanthrene. Each of those materials may have an aryl group, a heteroaromatic ring group, a diarylamino group, or an alkyl group as a substituent.

When the fluorescent light-emitting material is used as the fluorescent light-emitting dopant and the host material is incorporated, the amount of the fluorescent light-emitting dopant to be incorporated into the light-emitting layer desirably falls within the range of 0.01 to 20 wt %, preferably 0.1 to 10 wt %.

In the case where the light-emitting layer is a phosphorescent light-emitting layer, a phosphorescent light-emitting dopant and a host material are incorporated. It is recommended to use, as a material for the phosphorescent light-emitting dopant, a material containing an organic metal complex including at least one metal selected from ruthenium, rhodium, palladium, silver, rhenium, osmium, iridium, platinum, and gold. Such organic metal complexes are known in the prior art documents and the like, and a complex is selected therefrom and may be used.

Preferred examples of the phosphorescent light-emitting dopant include complexes such as $Ir(ppy)_3$, complexes such as $(Bt)_2$ Iracac, and complexes such as (Btp)Ptacac, the complexes each having a noble metal element such as Ir as a central metal. Specific examples of those complexes are shown below, but the complexes are not limited to the compounds described below.

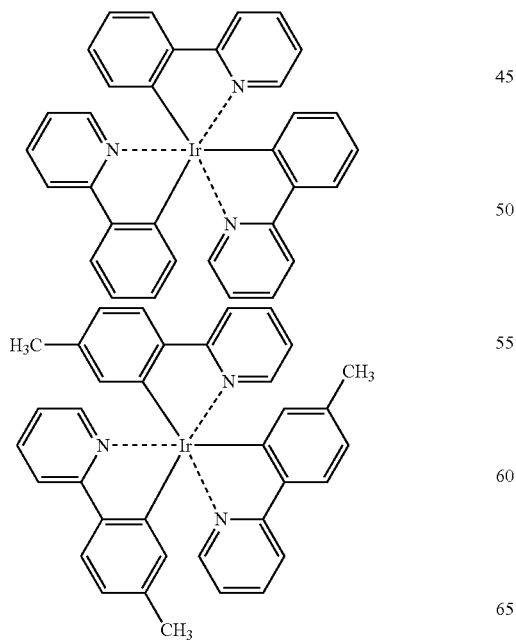

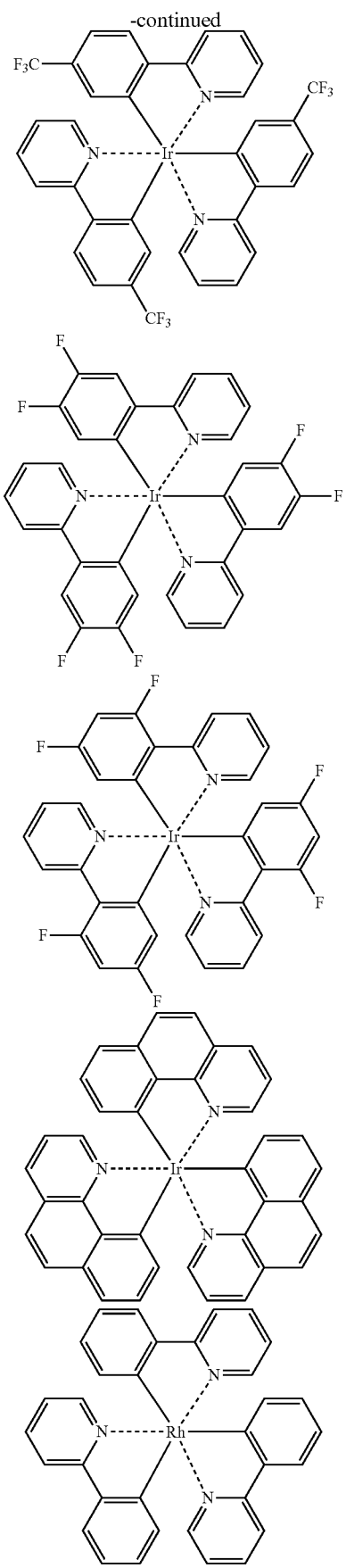

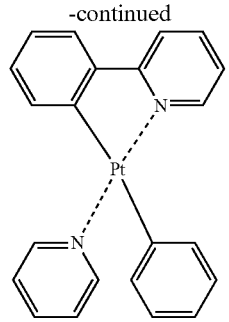
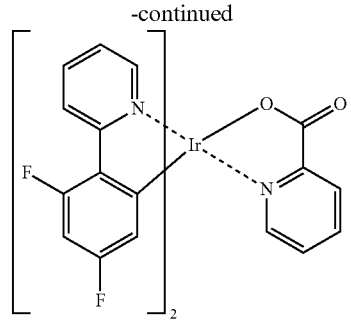
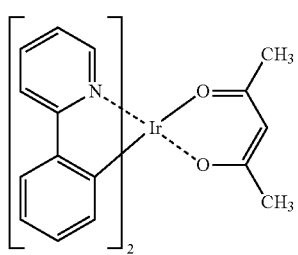
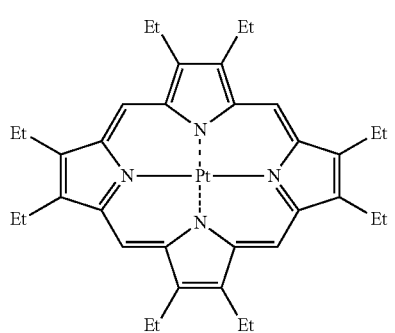
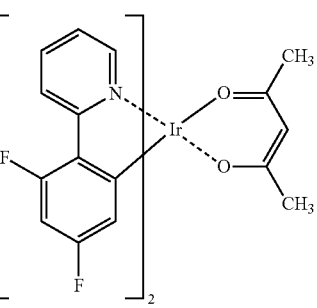
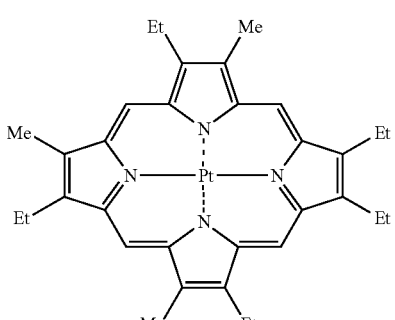
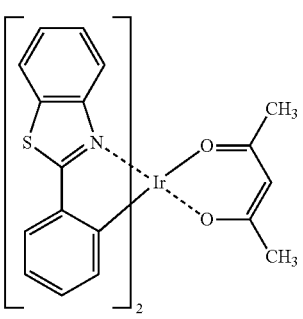
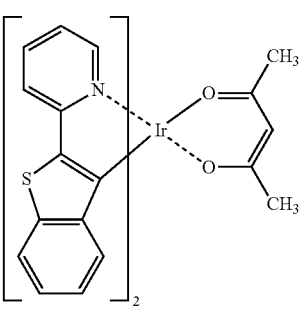
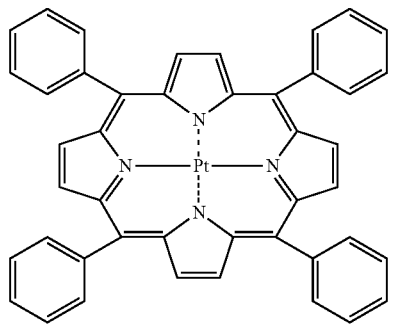

-continued

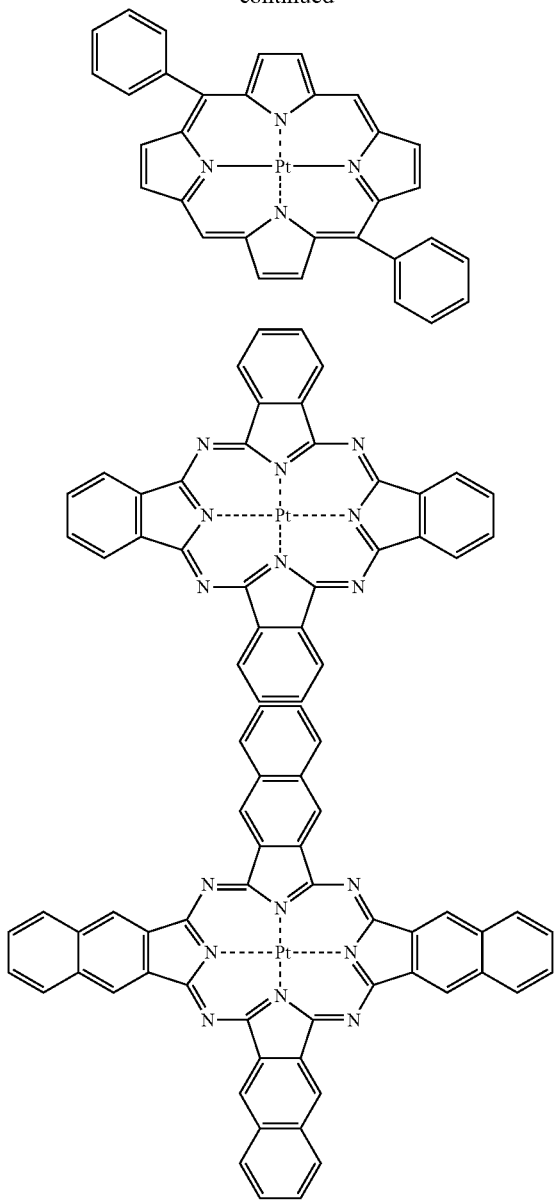

The content of the phosphorescent light-emitting dopant in the light-emitting layer is in the range of preferably 1 to 50 wt %, more preferably 5 to 30 wt %.

It is preferred to use, as a host material in the light-emitting layer, the compound represented by the general formula (1). However, when the nitrogen-containing aromatic compound is used in any of the organic layers other than the light-emitting layer, the material to be used in the light-emitting layer may be another host material other than the compound represented by the general formula (1), or the compound represented by the general formula (1) and any other host material may be used in combination. Further, a plurality of kinds of known host materials may be used in combination.

It is preferred to use, as a usable known host compound, a compound that has a hole-transporting ability or an electron-transporting ability, is capable of preventing luminescence from having a longer wavelength, and has a high glass transition temperature.

Such other host materials are known because they are mentioned in many patent literatures and the like, and hence a suitable host material may be chosen from those in the patent literatures and the like. Specific examples of the host material, which are not particularly limited, include an indole derivative, a carbazole derivative, a triazole derivative, an oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic dimethylidene-based compound, a porphyrine-based compound, an anthraquinodimethane derivative, an anthrone derivative, a diphenylquinone derivative, a thiopyrane dioxide derivative, a heterocyclic tetracarboxylic acid anhydride such as naphthalene perylene, a phthalocyanine derivative, various metal complexes typified by a metal complex of an 8-quinolinol derivative, a metal phthalocyanine, and metal complexes of benzoxazole and benzothiazole derivatives, and polymer compounds such as a polysilane-based compound, a poly(N-vinylcarbazole) derivative, an aniline-based copolymer, a thiophene oligomer, a polythiophene derivative, a polyphenylene derivative, a polyphenylenevinylene derivative, and a polyfluorene derivative.

—Injecting Layer—

The injecting layer refers to a layer provided between an electrode and an organic layer for the purpose of lowering a driving voltage and improving a light emission luminance, and includes a hole-injecting layer and an electron-injecting layer. The injecting layer may be interposed between the anode and the light-emitting layer or the hole-transporting layer, or may be interposed between the cathode and the light-emitting layer or the electron-transporting layer. The injecting layer may be provided as required.

—Hole-Blocking Layer—

The hole-blocking layer has, in a broad sense, the function of an electron-transporting layer, and is formed of a hole-blocking material that has a remarkably small ability to transport holes while having a function of transporting electrons, and hence the hole-blocking layer is capable of improving the probability of recombining an electron and a hole by blocking holes while transporting electrons.

It is possible to use the compound represented by the general formula (1) for the hole-blocking layer. However, when the compound is used in any other organic layer, a known material for a hole-blocking layer may be used. Further, it is possible to use, as a material for the hole-blocking layer, any of the below-mentioned materials for the electron-transporting layer as required.

—Electron-Blocking Layer—

The electron-blocking layer is formed of a material that has a remarkably small ability to transport electrons while having a function of transporting holes, and hence the electron-blocking layer is capable of improving the probability of recombining an electron and a hole by blocking electrons while transporting holes.

Although the compound represented by the general formula (1) is preferably used as a material for the electron-blocking layer, when the compound is used in any other organic layer, any of the below-mentioned materials for the hole-transporting layer can be used as required. The thickness of the electron-blocking layer is preferably 3 to 100 nm, more preferably 5 to 30 nm.

—Exciton-Blocking Layer—

The exciton-blocking layer refers to a layer used for blocking excitons produced by the recombination of a hole and an electron in the light-emitting layer from diffusing in charge-transporting layers. Inserting this layer enables effective confinement of the excitons in the light-emitting layer, thereby being able to improve the luminous efficiency of the device. The exciton-blocking layer may be inserted on any of the anode side and the cathode side of the adjacent light-emitting layer, and may also be inserted simultaneously on both sides.

Although the compound represented by the general formula (1) can be used as a material for the exciton-blocking layer, when the compound is used in any other organic layer, the material for the exciton-blocking layer is, for example, 1,3-dicarbazolylbenzene (mCP) or bis(2-methyl-8-quinolinolato)-4-phenylphenolatoaluminum(III) (BAlq).

—Hole-Transporting Layer—

The hole-transporting layer is formed of a hole-transporting material having a function of transporting holes, and a single hole-transporting layer or a plurality of hole-transporting layers may be provided.

The hole-transporting material has hole-injecting property or hole-transporting property or has electron-blocking property, and any of an organic compound and an inorganic compound may be used as the hole-transporting material. Although it is preferred to use the compound represented by the general formula (1) as the hole-transporting material, when the compound is used in any other organic layer, any compound selected from conventionally known compounds may be used. Examples of the known hole-transporting material which may be used include a triazole derivative, an oxadiazole derivative, an imidazole derivative, a polyarylalkane derivative, a pyrazoline derivative, and a pyrazolone derivative, a phenylenediamine derivative, an aromatic amine derivative, an amino-substituted chalcone derivative, an oxazole derivative, a styrylanthracene derivative, a fluorenone derivative, a hydrazone derivative, a stilbene derivative, a silazane derivative, an aniline-based copolymer, a porphyrin compound, a styrylamine compound, and a conductive high-molecular weight oligomer, in particular, a thiophene oligomer. However, a porphyrin compound, an aromatic tertiary amine compound, or a styrylamine compound is preferably used, and an aromatic tertiary amine compound is more preferably used.

—Electron-Transporting Layer—

The electron-transporting layer is formed of a material having a function of transporting electrons, and a single electron-transporting layer or a plurality of electron-transporting layers may be provided.

An electron-transporting material (which also serves as a hole-blocking material in some cases) has only to have a function of transferring electrons injected from the cathode into the light-emitting layer. Although it is preferred to use the compound represented by the general formula (1) for the electron-transporting layer, when the compound is used in any other organic layer, any compound selected from conventionally known compounds may be used. Examples thereof include a nitro-substituted fluorene derivative, a diphenylquinone derivative, a thiopyran dioxide derivative, carbodiimide, a fluorenylidenemethane derivative, anthraquinodimethane, an anthrone derivative, and an oxadiazole derivative. Further, it is also possible to use, as the electron-transporting material, a thiadiazole derivative prepared by substituting an oxygen atom on an oxadiazole ring with a sulfur atom in the oxadiazole derivative and a quinoxaline derivative which has a quinoxaline ring known as an electron withdrawing group. Further, it is also possible to use a polymer material in which any of those materials is introduced in a polymer chain or is used as a polymer main chain.

EXAMPLES

Hereinafter, the present invention is described in more detail with reference to examples. It should be appreciated that the present invention is not limited to these examples and may be carried out in various forms as long as the various forms do not deviate from the gist of the present invention.

The routes described below were used to synthesize the compound represented by the general formula (1). It should be noted that the number of each compound corresponds to the number given to each chemical formula described above.

Synthesis Example 1

Synthesis of Compound 1-1

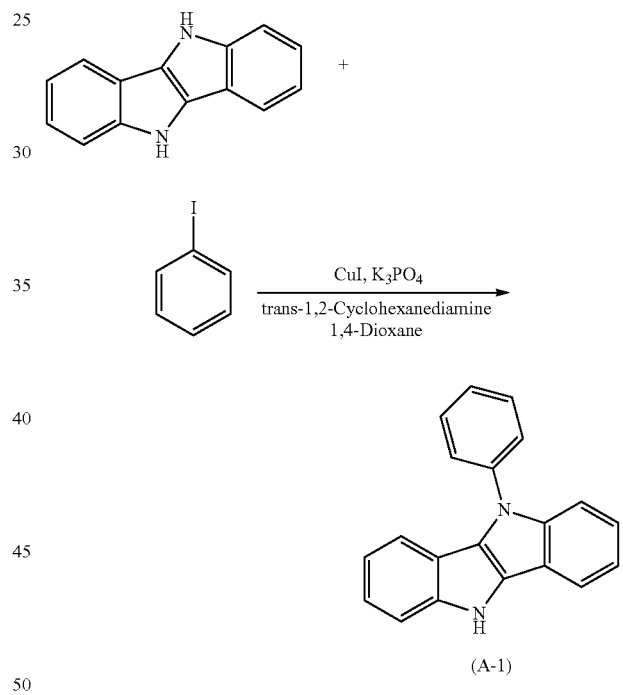

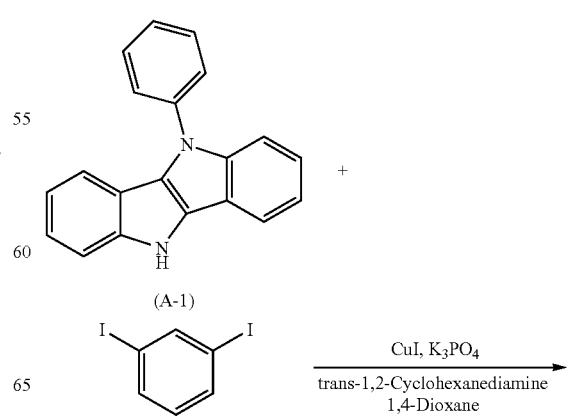

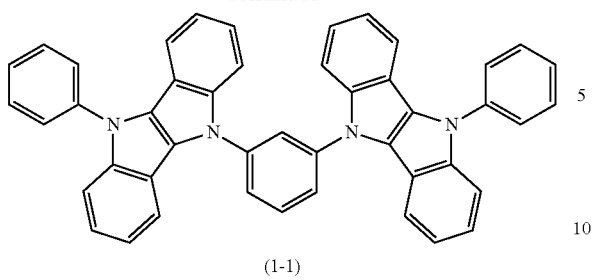

(1-1)

Under a nitrogen atmosphere, 20 g (97 mmol) of indolo[3,2-b]indole, 19 g (93 mmol) of iodobenzene, 1.7 g (8.9 mmol) of copper iodide, 59 g (278 mmol) of tripotassium phosphate, 11 g (96 mmol) of trans-1,2-cyclohexanediamine, and 500 ml of 1,4-dioxane were loaded, and then the mixture was stirred for 4 hours while being heated at 120° C. After the reaction solution had been cooled to room temperature, a precipitated crystal was taken by filtration and then the solvent was distilled off under reduced pressure. The resultant residue was purified by silica gel column chromatography to provide 14 g (49 mmol, 53 mol % yield) of an intermediate A-1.

Under a nitrogen atmosphere, 4.0 g (14 mmol) of the intermediate A-1, 2.4 g (7.3 mmol) of 1,3-diiodobenzene, 0.68 g (3.6 mmol) of copper iodide, 23 g (106 mmol) of tripotassium phosphate, 4.0 g (39 mmol) of trans-1,2-cyclohexanediamine, and 100 ml of 1,4-dioxane were loaded, and then the mixture was stirred for 16 hours while being heated at 120° C. After the reaction solution had been cooled to room temperature, a precipitated crystal was taken by filtration and then the solvent was distilled off under reduced pressure. The resultant residue was purified by silica gel column chromatography to provide 3.5 g (5.5 mmol, 75 mol % yield) of a compound 1-1 as a white solid.

Synthesis Example 2

Synthesis of Compound 2-1

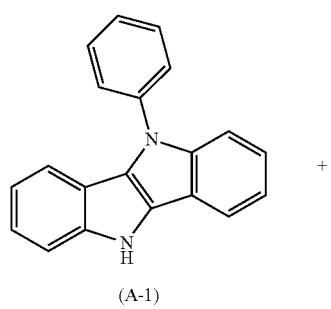

(A-1)

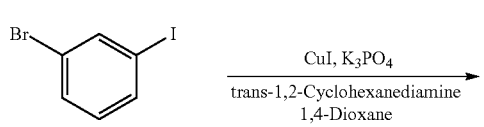

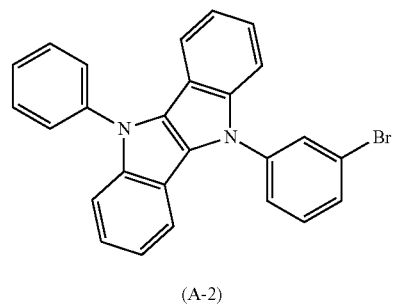

(A-2)

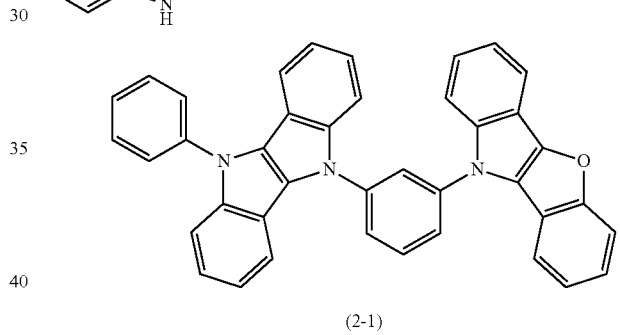

Under a nitrogen atmosphere, 13.0 g (46 mmol) of the intermediate A-1, 13 g (46 mmol) of 1-bromo-3-iodobenzene, 0.87 g (4.6 mmol) of copper iodide, 29 g (137 mmol) of tripotassium phosphate, 5.2 g (46 mmol) of trans-1,2-cyclohexanediamine, and 400 ml of 1,4-dioxane were loaded, and then the mixture was stirred for 4 hours while being heated at 120° C. After the reaction solution had been cooled to room temperature, a precipitated crystal was taken by filtration and then the solvent was distilled off under reduced pressure. The resultant residue was purified by silica gel column chromatography to provide 11 g (25 mmol, 54 mol % yield) of an intermediate A-2.

Under a nitrogen atmosphere, 4.0 g (9.1 mmol) of the intermediate A-2, 1.9 g (9.2 mmol) of benzofuro[3,2-b]indole, 0.18 g (0.95 mmol) of copper iodide, 5.9 g (28 mmol) of tripotassium phosphate, 1.0 g (8.8 mmol) of trans-1,2-cyclohexanediamine, and 90 ml of 1,4-dioxane were loaded, and then the mixture was stirred for 18 hours while being heated at 120° C. After the reaction solution had been cooled to room temperature, a precipitated crystal was taken by filtration and then the solvent was distilled off under reduced pressure. The resultant residue was purified by silica gel column chromatography to provide 4.1 g (7.3 mmol, 80 mol % yield) of a compound 2-1 as a white solid.

Synthesis Example 3

Synthesis of Compound 3-1

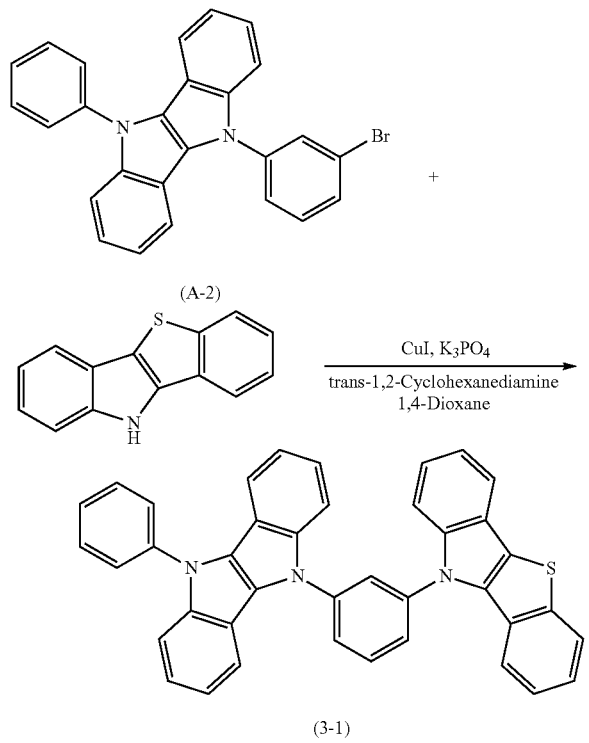

Under a nitrogen atmosphere, 4.0 g (9.1 mmol) of the intermediate A-2, 2.0 g (9.1 mmol) of benzothieno[3,2-b]indole, 0.18 g (0.95 mmol) of copper iodide, 5.9 g (28 mmol) of tripotassium phosphate, 1.0 g (8.8 mmol) of trans-1,2-cyclohexanediamine, and 90 ml of 1,4-dioxane were loaded, and then the mixture was stirred for 24 hours while being heated at 120° C. After the reaction solution had been cooled to room temperature, a precipitated crystal was taken by filtration and then the solvent was distilled off under reduced pressure. The resultant residue was purified by silica gel column chromatography to provide 3.8 g (6.6 mmol, 73 mol % yield) of a compound 3-1 as a white solid.

In addition, compounds 1-5, 1-7, 1-9, and 1-12 were synthesized in conformity with the synthesis methods described in the synthesis examples and the description, and were then used in the production of organic EL devices.

Example 1

Each thin film was laminated by a vacuum deposition method at a degree of vacuum of $4.0 \times 10^{-5}$ Pa on a glass substrate on which an anode formed of an ITO having a thickness of 110 nm had been formed. First, copper phthalocyanine (CuPC) was formed into a layer having a thickness of 25 nm on the ITO. Next, 4,4'-bis[N-(1-naphthyl)-N-phenylamino]biphenyl (NPB) was formed into a layer having a thickness of 55 nm to serve as a hole-transporting layer. Next, the compound 1-1 obtained in Synthesis Example 1 as a host material and bis(2-(2'-benzo[4,5-a]thienyl)pyridinato-N,C3) iridium(acetylacetonate) ((Btp)2Iracac) as a phosphorescent light-emitting dopant were co-deposited from different deposition sources onto the hole-transporting layer to form a light-emitting layer having a thickness of 47.5 nm. The concentration of (Btp)$_2$Iracac in the light-emitting layer was 8.0 wt %. Next, tris(8-hydroxyquinolinato)aluminum(III) (Alq3) was formed into a layer having a thickness of 30 nm to serve as an electron-transporting layer. Further, lithium fluoride (LiF) was formed into a layer having a thickness of 1.0 nm on the electron-transporting layer to serve as an electron-injecting layer. Finally, aluminum (Al) was formed into a layer having a thickness of 200 nm on the electron-injecting layer to serve as an electrode. Thus, an organic EL device was produced.

An external power source was connected to the resultant organic EL device to apply a DC voltage to the device. As a result, the device was observed to have such light-emitting characteristics as shown in Table 1. The columns "luminance," "voltage," and "luminous efficiency" in Table 1 show values at 10 mA/cm$^2$. It should be noted that it was found that the local maximum wavelength of the emission spectrum of the device was 620 nm and hence light emission from (Btp)$_2$Iracac was obtained.

Example 2

An organic EL device was produced in the same manner as in Example 1 except that the compound 2-1 was used as the host material for the light-emitting layer.

Example 3

An organic EL device was produced in the same manner as in Example 1 except that the compound 3-1 was used as the host material for the light-emitting layer.

Example 4

An organic EL device was produced in the same manner as in Example 1 except that the compound 1-5 was used as the host material for the light-emitting layer.

Example 5

An organic EL device was produced in the same manner as in Example 1 except that the compound 1-7 was used as the host material for the light-emitting layer.

Example 6

An organic EL device was produced in the same manner as in Example 1 except that the compound 1-9 was used as the host material for the light-emitting layer.

Example 7

An organic EL device was produced in the same manner as in Example 1 except that the compound 1-12 was used as the host material for the light-emitting layer.

Comparative Example 1

An organic EL device was produced in the same manner as in Example 22 except that bis(2-methyl-8-quinolinolato)-4-phenylphenolatoaluminum(III) (BAlq) was used as the host material for the light-emitting layer.

Comparative Example 2

An organic EL device was produced in the same manner as in Example 1 except that the following compound H-1 was used as the host material for the light-emitting layer.

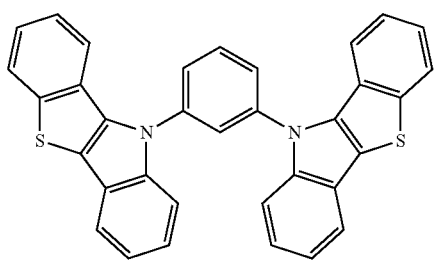

It was found that the local maximum wavelength of the emission spectrum of each of the organic EL devices produced in Examples 2 to 7 and Comparative Examples 1 and 2 was 620 nm and hence light emission from (Btp)$_2$Iracac was obtained. Table 1 shows the light-emitting characteristics and lifetime characteristics.

TABLE 1

| | | Light-emitting characteristic (@10 mA/cm$^2$) | | |
|---|---|---|---|---|
| | Compound | Luminance (cd/m$^2$) | Voltage (V) | Visual luminous efficiency (1 m/W) |
| Example | | | | |
| 1 | 1-1 | 1302 | 5.0 | 6.7 |
| 2 | 2-1 | 1121 | 6.2 | 4.1 |
| 3 | 3-1 | 1159 | 7.2 | 3.8 |
| 4 | 1-5 | 1279 | 5.9 | 6.1 |
| 5 | 1-7 | 1202 | 7.1 | 3.9 |
| 6 | 1-9 | 1386 | 7.8 | 5.1 |
| 7 | 1-12 | 1240 | 5.9 | 5.9 |
| Comparative Example | | | | |
| 1 | BAlq | 1020 | 8.4 | 3.8 |
| 2 | H-1 | 1090 | 8.5 | 3.5 |

Table 1 shows that the nitrogen-containing aromatic compound represented by the general formula (1) to be used in the organic EL device of the present invention shows good light-emitting characteristics as compared with BAlq generally known as a phosphorescent host. In addition, the nitrogen-containing aromatic compound shows good light-emitting characteristics as compared with the H-1 as a compound free of an indolo[3,2-b]indole skeleton in a molecule thereof, and hence the superiority of the compound is apparent.

INDUSTRIAL APPLICABILITY

The nitrogen-containing aromatic compound of the present invention may enable the control of various energy values, i.e., an ionization potential, an electron affinity, and a triplet excitation energy because its skeleton has one or more indolo[3,2-b]indole skeletons. In addition, the presence of a plurality of indolo[3,2-b]indole skeletons may improve stability against charge. In addition, the nitrogen-containing aromatic compound of the present invention may have a high charge-transferring characteristic. Therefore, an organic electroluminescent device using the nitrogen-containing aromatic compound of the present invention may be able to express high characteristics. In addition, the nitrogen-containing aromatic compound of the present invention may find applications in, for example, displays such as electronic paper, liquid crystal displays, organic field-effect transistors, organic thin-film solar cells, information tags, and large-area sensors such as an electronic artificial skin sheet and a sheet-type scanner as well as organic EL devices, and hence its technical value is large.

The invention claimed is:

1. An organic electroluminescent device, comprising an anode, a plurality of organic layers, and a cathode laminated on a substrate, wherein at least one of the organic layers contains a compound represented by the general formula (1):

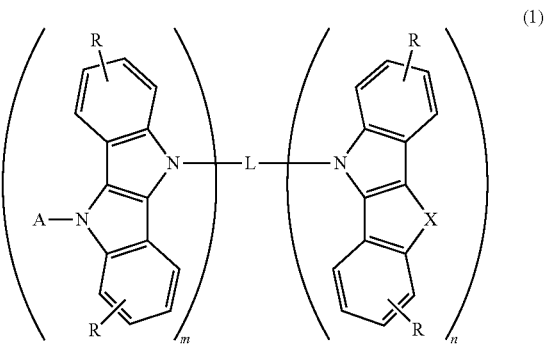

(1)

in the formula, L represents an n+m-valent group arising from an alkane having 1 to 30 carbon atoms, a cycloalkane having 3 to 30 carbon atoms, an aromatic hydrocarbon having 6 to 50 carbon atoms, an aromatic heterocyclic compound having 3 to 50 carbon atoms and free of a fused heterocycle having 4 or more rings, a triarylamine having 9 to 30 carbon atoms, or a diarylsulfone having 6 to 24 carbon atoms; A's each independently represent an alkyl group having 1 to 30 carbon atoms, a cycloalkyl group having 3 to 30 carbon atoms, an alkenyl group having 2 to 30 carbon atoms, an alkynyl group having 2 to 30 carbon atoms, a silyl group having 3 to 18 carbon atoms, an acyl group having 2 to 19 carbon atoms, an aromatic hydrocarbon group having 6 to 50 carbon atoms, or an aromatic heterocyclic group having 3 to 50 carbon atoms and free of a fused heterocycle having 4 or more rings; X's each independently represent oxygen or sulfur; R's each independently represent hydrogen, an alkyl group having 1 to 30 carbon atoms, a cycloalkyl group having 3 to 30 carbon atoms, an alkenyl group having 2 to 30 carbon atoms, an alkynyl group having 2 to 30 carbon atoms, an aromatic hydrocarbon group having 6 to 30 carbon atoms, or an aromatic heterocyclic group having 3 to 30 carbon atoms and free of a fused heterocycle having 4 or more rings; m represents an integer of 1 to 4; n represents an integer of 0 to 3; and a total number of m and n is 2 to 4.

2. An organic electroluminescent device according to claim 1, wherein the compound represented by the general formula (1) is represented by the formula (2):

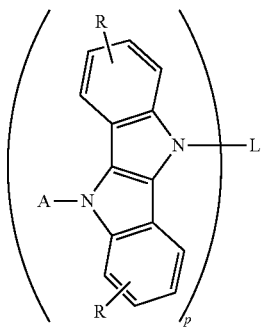

(2)

in the formula (2), L, A, and R's each have the same meaning as that in the general formula (1), and p represents an integer of 2 to 4.

3. An organic electroluminescent device according to claim 2, wherein p in the general formula (2) represents 2 or 3.

4. An organic electroluminescent device according to claim 1, wherein the layer which contains the compound represented by the general formula (1) comprises at least one layer selected from the group consisting of a light-emitting layer, a hole-transporting layer, and an electron-blocking layer.

5. An organic electroluminescent device according to claim 4, wherein the layer which contains the compound represented by the general formula (1) comprises the light-emitting layer containing a phosphorescent light-emitting dopant.

6. An organic electroluminescent device according to claim 2, wherein the layer which contains the compound represented by the general formula (1) comprises at least one layer selected from the group consisting of a light-emitting layer, a hole-transporting layer, and an electron-blocking layer.

7. An organic electroluminescent device according to claim 3, wherein the layer which contains the compound represented by the general formula (1) comprises at least one layer selected from the group consisting of a light-emitting layer, a hole-transporting layer, and an electron-blocking layer.

8. An organic electroluminescent device according to claim 6, wherein the layer which contains the compound represented by the general formula (1) comprises the light-emitting layer containing a phosphorescent light-emitting dopant.

9. An organic electroluminescent device according to claim 7, wherein the layer which contains the compound represented by the general formula (1) comprises the light-emitting layer containing a phosphorescent light-emitting dopant.

10. An organic electroluminescent device according to claim 1, wherein n in the general formula (1) represents an integer of 1 to 3.

* * * * *